US006607700B1

(12) United States Patent
Apte et al.

(10) Patent No.: US 6,607,700 B1
(45) Date of Patent: Aug. 19, 2003

(54) GAS DIFFUSION SAMPLING AND MEASUREMENT SYSTEM FOR OCCUPATIONAL DOSIMETRY AND AIR QUALITY MONITORING AS EXEMPLIFIED BY A CARBON MONOXIDE OCCUPATIONAL DOSIMETER

(75) Inventors: Michael G. Apte, Berkeley, CA (US); Mark K. Goldstein, Del Mar, CA (US); Michelle S. Oum, Chula Vista, CA (US); William B. Helfman, Chula Vista, CA (US)

(73) Assignee: Quantum Group, Inc., San Diego, CA (US)

( * ) Notice: Subject to any disclaimer, the term of this patent is extended or adjusted under 35 U.S.C. 154(b) by 0 days.

(21) Appl. No.: 09/350,699

(22) Filed: Jul. 9, 1999

(51) Int. Cl.$^7$ ............................................... G01N 17/00
(52) U.S. Cl. .................... 422/91; 422/68.1; 422/50; 422/52; 422/55; 422/56; 422/58; 73/23.37; 436/134; 436/164
(58) Field of Search ................... 422/91, 82.05, 422/104, 50, 52, 55, 56, 57, 58, 68.1, 69, 83, 85, 88; 436/134, 164; 73/23.37, 24.02

(56) References Cited

U.S. PATENT DOCUMENTS

| | | | | |
|---|---|---|---|---|
| 4,668,635 A | * | 5/1987 | Forster | 436/134 |
| 4,803,052 A | * | 2/1989 | Abromaitis et al. | 422/91 |
| 5,063,164 A | | 11/1991 | Goldstein | 436/169 |
| 5,618,493 A | * | 4/1997 | Goldstein et al. | 422/57 |
| 5,691,465 A | * | 11/1997 | Carr et al. | 73/24.02 |
| 5,733,505 A | | 3/1998 | Goldstein et al. | 422/83 |
| 5,980,832 A | * | 11/1999 | Andresen et al. | 422/91 |
| 6,096,560 A | * | 8/2000 | Scripca et al. | 436/164 |

* cited by examiner

*Primary Examiner*—Jill Warden
*Assistant Examiner*—Brian Sines
(74) *Attorney, Agent, or Firm*—Christie, Parker & Hale, LLP

(57) ABSTRACT

CO exposure is a serious public health problem in the U.S., causing both morbidity and mortality (lifetime mortality risk approximately $10^{-4}$). Sparse data from population-based CO exposure assessments indicate that approximately 10% of the U.S. population is exposed to CO above the National Ambient Air Quality Standard. No CO exposure measurement technology is available for affordable population-based CO exposure assessment studies.

Two CO measuring devices, an occupational CO dosimeter (LOCD) and an indoor air quality (IAQ) passive sampler, were designed, developed, and tested both in the laboratories and field. Time-weighted-average CO exposure of the compact diffusion tube sampler containing a selective and non-regenerative palladium-molybdenum based CO sensor is quantified by using a simple spectrophotometer.

Both devices are capable of measuring CO exposure precisely with relative standard deviation of less than 20% and with bias of less than 10%. Results indicated that the CO exposure distributions measured by LOCD has a precison of about +/−1 ppm.

13 Claims, 20 Drawing Sheets

| Step 1: | The homogeneous water-gas shift reaction via the intermediacy of palladium. | | |
|---|---|---|---|
| (forward) | $PdCl_4^{2-} + CO \xrightleftharpoons[k_{-1}]{k_1} PdCl_3(CO)^- + Cl^-$ | | 1a |
| | $PdCl_3(CO)^- + H_2O \xrightarrow{k_2} PdCl_3(CO_2H)^{2-} + H^+$ | | 1b |
| | $PdCl_3(CO_2H)^{2-} \xrightarrow{fast} Pd(0) + 3Cl^- + H^+ + CO_2$ | | 1c |
| Step 2: | The reduction by Pd(0) of Mo(VI) to mixed valent molybdenum species with an intense blue color, molybdenum blue. Note: possible competitive reaction when copper is present.<br>(Measured Analyte) | | |
| (forward) | $Pd(0) + 2/x\,MoO_3 + 2H^+ \xrightleftharpoons[k_{-3}]{k_3} Pd(II) + 2/x\,[H_xMo O_3]_{Blue}$ | | 2a ($0 < x \le 1.05$) |
| | $Pd(0) + 2Cu(II) \longrightarrow Pd(II) + 2Cu(I)$ | (competitive reaction) | |
| Step 3: | Oxidation of the molybdenum blue species by Cu(II) or $O_2$. | | |
| (reverse) | $1/x\,[H_xMoO_3]_{Blue} + Cu(II) \xrightarrow{H^+} 1/x\,MoO_3 + H^+ + Cu(I)$ | | 3a (catalytic) |
| | $1/x\,[H_xMoO_3]_{Blue} + \tfrac{1}{2}O_2 + H^+ \xrightarrow{k_5} 1/x\,MoO_3 + H_2O$ | | 3b (direct) |
| Step 4: | Air oxidation of Cu(I) to give Cu(II) and water. | | |
| (reverse) | $CuCl_2^- + O_2 \longrightarrow CuCl_2(O_2)^-$ | | 4a |
| | $CuCl_2(O_2)^- + 4H^+ \longrightarrow Cu(II) + 2H_2O + 2Cl^-$ | | 4b |

FIG. 3

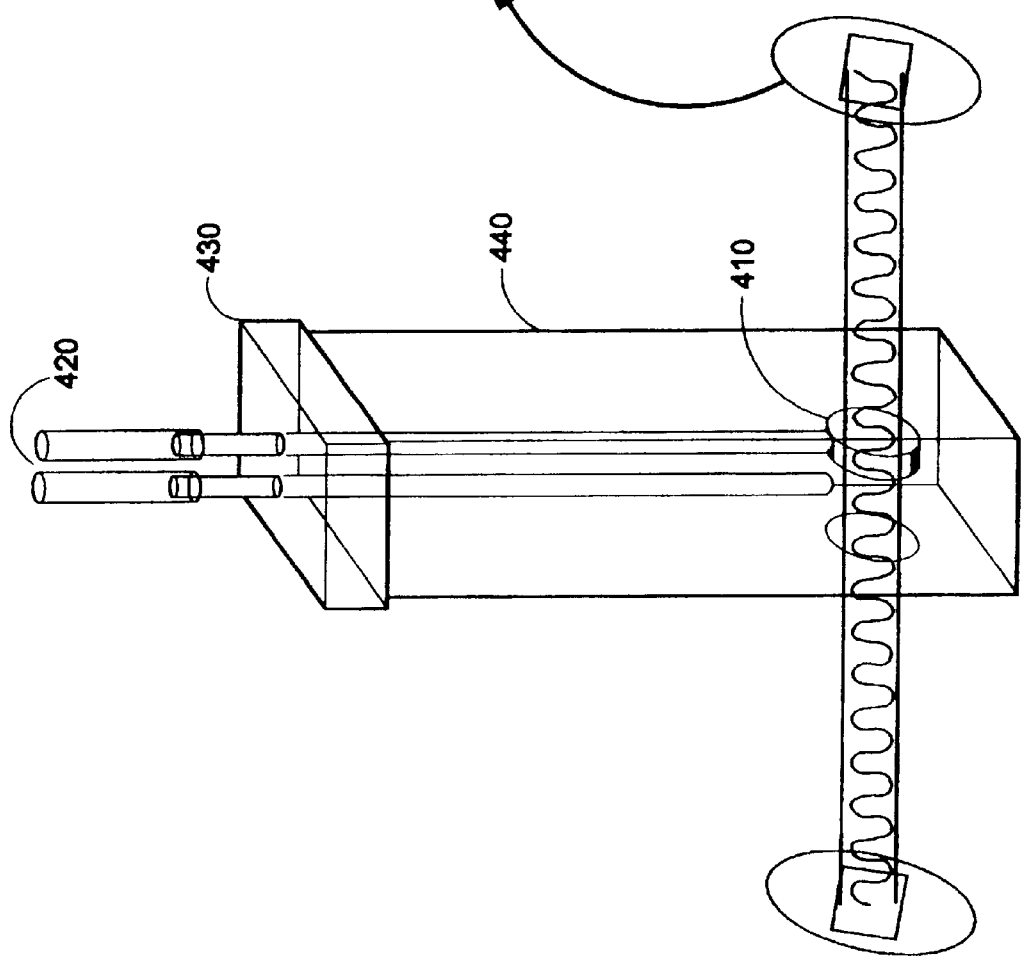
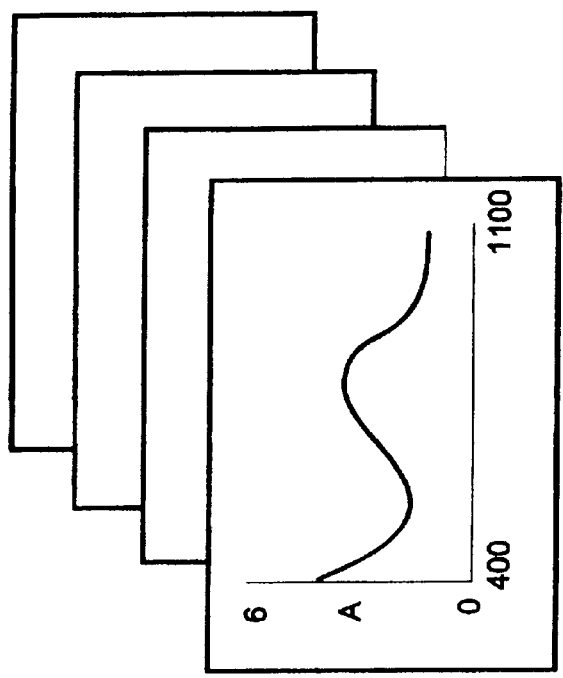
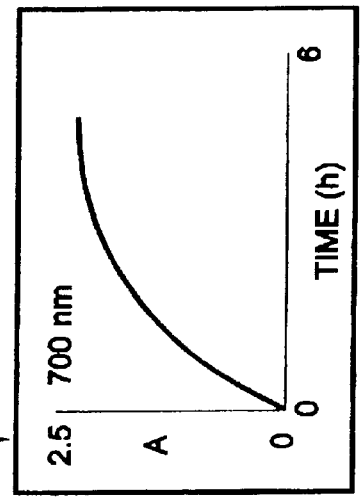

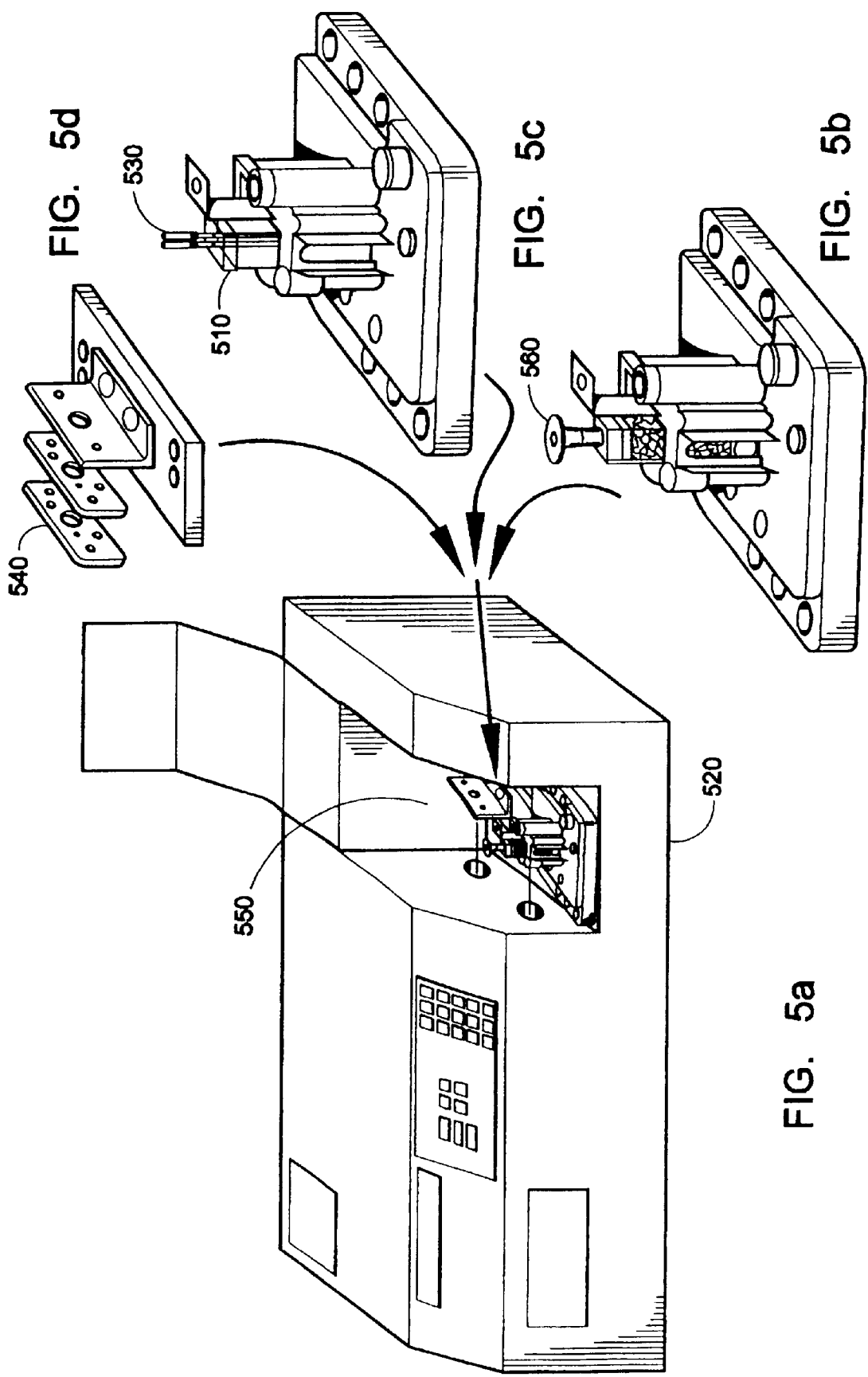

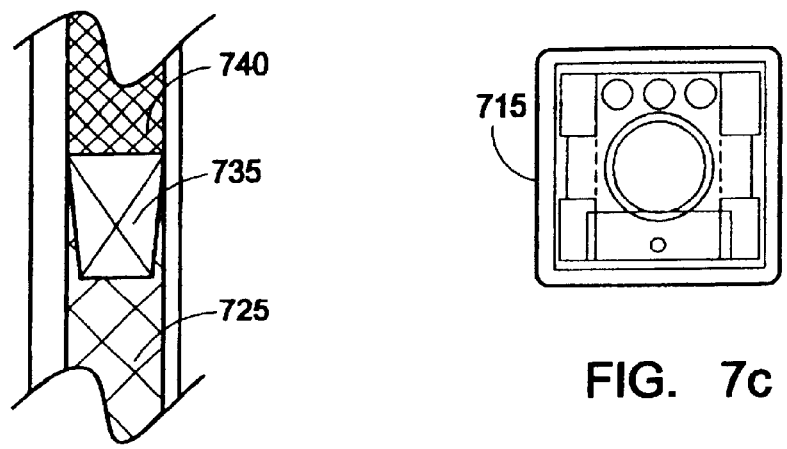
FIG. 7c
FIG. 7d
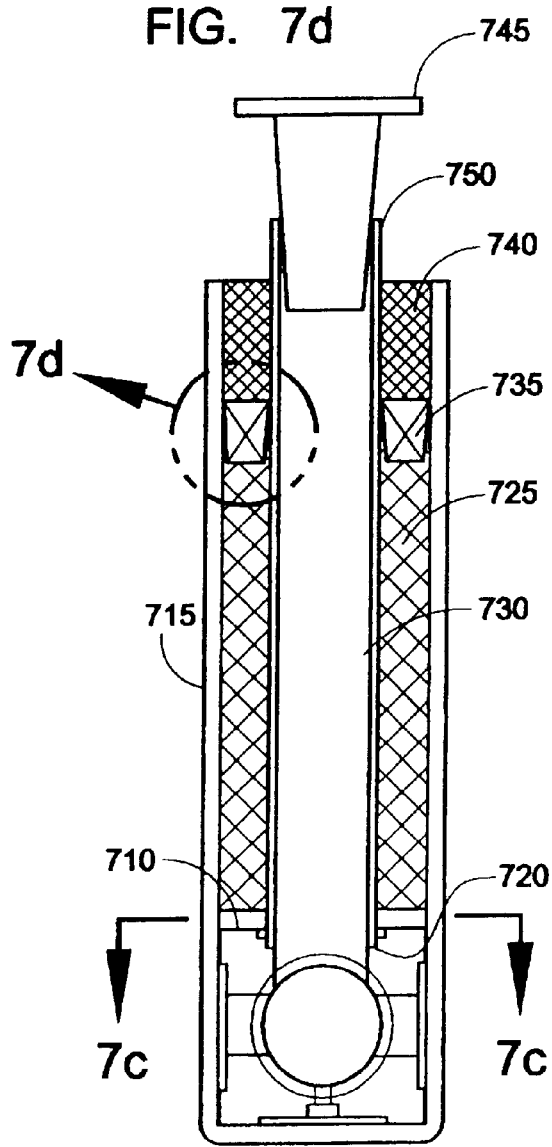
FIG. 7a
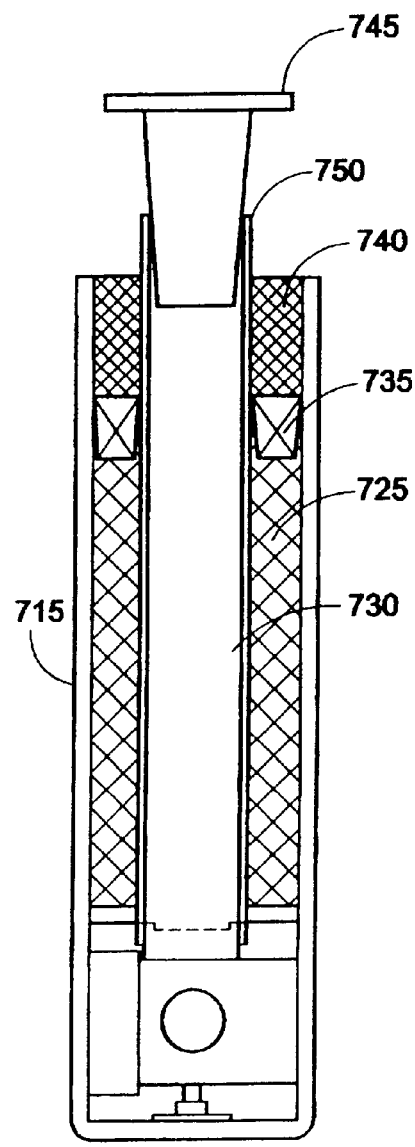
FIG. 7b

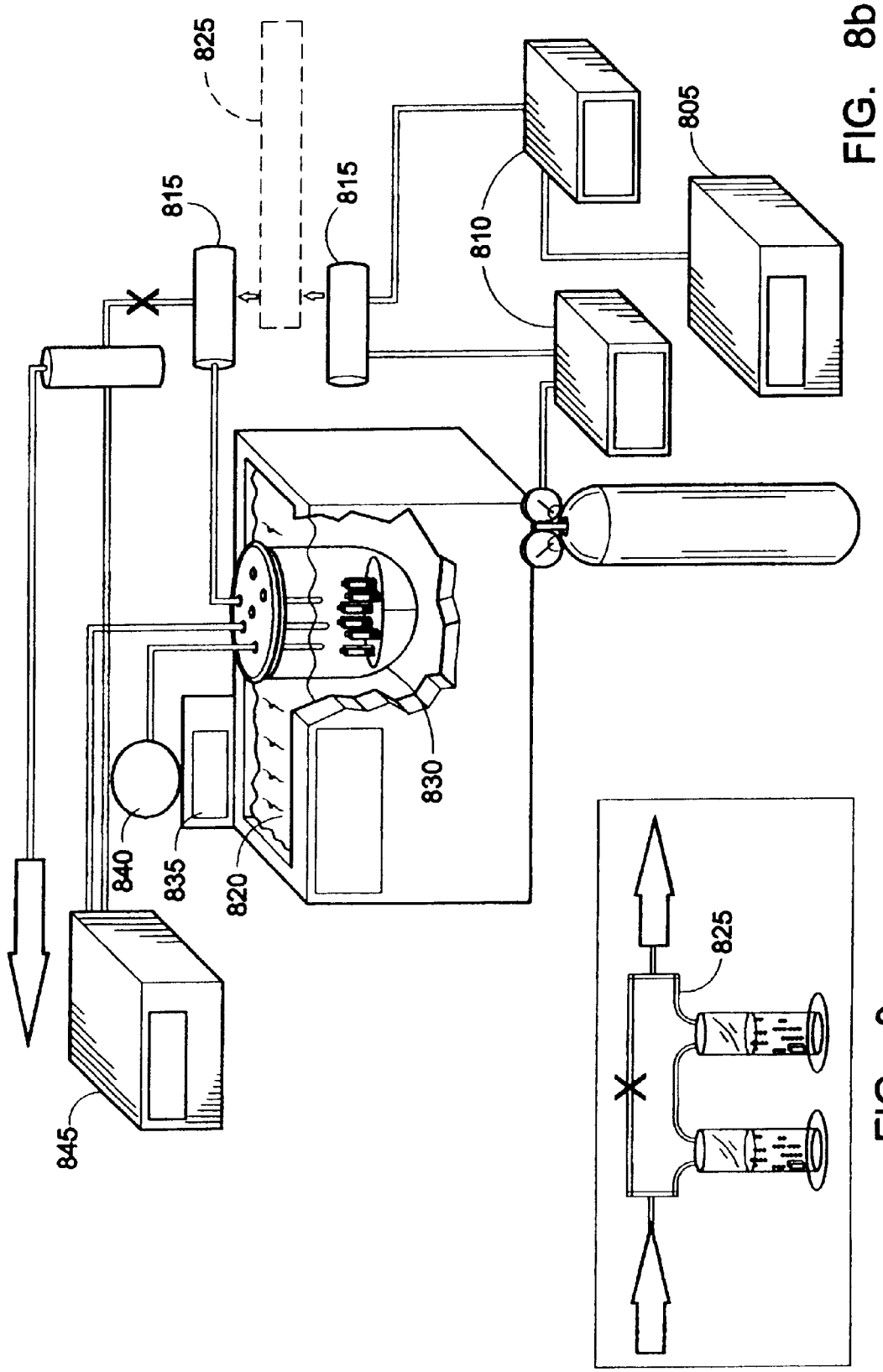

GAS DIFFUSION SAMPLING AND MEASUREMENT SYSTEM FOR OCCUPATIONAL DOSIMETRY AND AIR QUALITY MONITORING AS EXEMPLIFIED BY A CARBON MONOXIDE OCCUPATIONAL DOSIMETER

FIELD OF THE INVENTION

The present invention relates to two low-cost devices for quantitative measurements of gaseous constituents in ambient air. The measurement system integrates diffusive gas sampling technology with spectrophotometric analysis into a single package which can be reused and re-analyzed numerous times. An example of this system is a carbon monoxide occupational dosimeter (LOCD) and indoor air quality (IAQ) passive sampler. This invention is a result of a collaborative effort between Lawrence Berkeley National Laboratories (LBNL) and Quantum Group, Inc., CRADA No. BG94-204(00).

BACKGROUND OF THE INVENTION

A need exists for a passive sampler for population-based exposure assessment, particularly a dosimeter for the measurement of workplace and residential exposures to carbon monoxide.

An inexpensive occupational dosimeter that is, designed to measure CO exposure during an 8-hour work shift and an inexpensive passive sampler capable of measuring one-week average indoor CO concentrations in residences were developed. The devices use a simple quantitative method to assess time-weighted-average (TWA) workplace or residential exposures to CO. The device provides researchers and industrial hygienists with a means to conduct cost effective surveys of occupational CO exposures and residential indoor air quality studies.

The occupational dosimeter should be capable of measuring time weighted CO concentrations ranging from 10 to 800 parts-per-million-hours (ppm-h), i.e., 8-hour work-shift TWA CO concentrations of 1 to 100 ppm. An accuracy of ±20% and a precision of ±10 ppm-h at exposures above 40 ppm-h is required. These sampling ranges are appropriate for CO exposure assessment based upon the permissible levels set by regulatory bodies. The current Personal Exposure Limit (PEL) set by the U.S. Occupational Safety and Health Administration (OSHA, 1993) is 50 parts per million measured as a time-weighed-average (TWA) over 8-hours. The National Institute for Occupational Safety and Health (NIOSH) recommends an exposure limit of 35 ppm TWA for 8-hours (NIOSH, 1972), and the American Conference of Governmental Industrial Hygienists recommends a Threshold Limit Value (TLV) of 25 ppm TWA for 8-hours (ACGIH, 1991].

Conceptually, the passive sampler and the occupational dosimeter both operate on the principle of gas diffusion sampling (Rose, 1982; Palmes, 1976). They require no pump. CO reacts on the surface of the sensor so that the surface CO concentration is close to zero. In the LBNL/QGI diffusion sampler design the sensor is encased in a small vessel, with a tube that communicates from the inside, at the sensor surface, to the outside air. A removable plug at the opening of the tube is used to control CO diffusion to the sensor. Since the CO concentration ([CO]) at the sensor surface is zero, a CO partial pressure gradient exists along the tube, from CO laden environmental air to the sensor. When the plug is removed, this partial pressure gradient drives a diffusive flow of CO along the tube to react at the surface of the sensor. As the sensor reacts with CO, it changes color in a manner that can be used to assess CO exposure quantitatively. The sampling period is defined as the period for which the sampler's plug is removed from the diffusion tube.

SUMMARY OF THE INVENTION

A need exists for low-cost methods of quantitative determination of gas-phase constituents of ambient atmospheres. The measurement system described in this document integrates diffusive gas sampling technology with spectrophotometric analysis into a single package which can be reused and re-analyzed. This invention covers both the general sampling and measurement system and the carbon monoxide dosimeter and indoor air quality passive sampler.

BRIEF DESCRIPTION OF THE DRAWINGS

FIG. 3. Key elements of the QGI carbon monoxide sensor chemistry. The proprietary QGI CO sensor technology is based upon the following set of four discrete chemical steps. Although QGI's "MD" sensor series used in the LBNL/QGI CO dosimeter follows the chemistry presented here, the actual formulation is more complicated, involving molecular encapsulants and a Cu chelating process that deactivates the reverse reactions (steps 3 and 4). Further details of the chemistry are available in the literature (Goldstein, 1991a, 1991b). Modified from Goldstein et al., 1991.

FIGS. 4a, 4b and 4c. Diagram of a flow-through sensor holder for use in the Direct Method tests, and related graphs. These tests monitor QGI sensor response to CO in real-time, and are useful in determining CO sensor characteristics. The sensor holder is placed in a spectrometer light beam.

FIGS. 5a, 5b, 5c and 5d. Diagrams depicting three different systems for measuring the absorbance spectra of the QGI CO sensor. All three holders were designed to be fit into the light path of the spectrophotometer with the sensor positioned in the light beam. The Single Scan Sensor Holder (540) was used to measure sensor absorbance where single measurements were needed. The Direct Test Flow Through Sensor Holder (530) was used for real-time monitoring of sensor response in the flow-through exposure system. The Dosimeter Holder (560) was used for measuring the absorbance of sensors in situ in the LBNL/QGI Passive Samplers and Occupational Dosimeters.

FIGS. 7a, 7b, 7c and 7d. Engineering designs of the invention.

FIGS. 8a and 8b. Diagrams of laboratory exposure system for testing CO diffusion samplers.

Not shown in FIG. A is an attachment system comprised of an integrated clip potted into the top of the sampler assembly used as a hanger to accept a Snap-On strap with attached lapel clip. This is used for attachment of the device to clothing or subjects for personal sampling, or attachment of the sampler to other objects for area sampling.

DETAILED DESCRIPTION OF THE INVENTION

Figure 1:
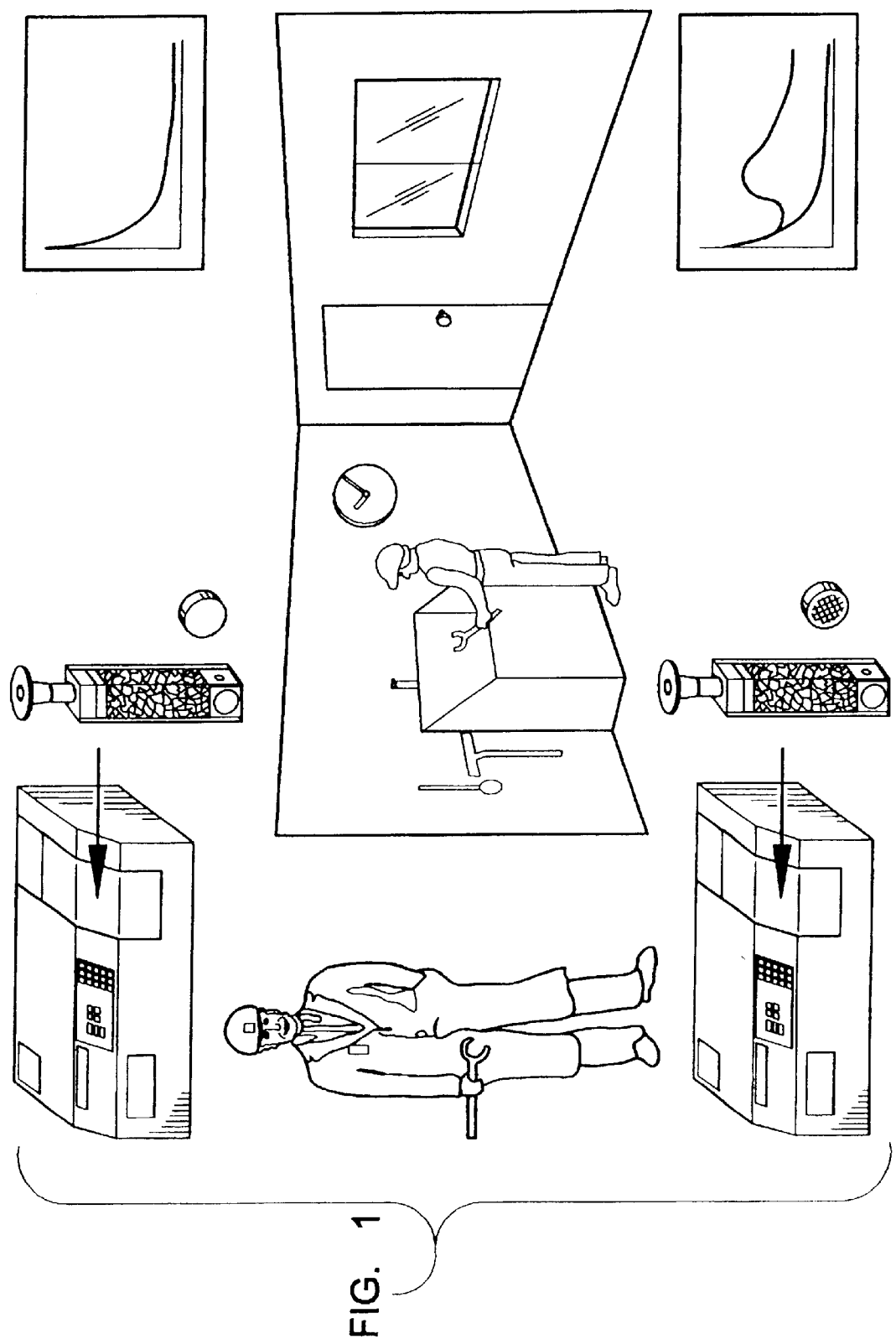
FIG. 1. Conceptual Design of Use of Sampler for Occupational or Indoor Air Quality Sampling.

The present invention is comprised of a measurement system for passive diffusive sampling, quantizing, and analyzing gaseous constituents (FIG. 1). The non-regenerating carbon monoxide sensors were integrated into the samplers (FIG. 2) to demonstrate reliability and the accuracy of this system. The fabrication of these sensors is described in U.S. Pat. No. 5,733,505 issued on Mar. 31, 1998. The sensors were stored with pre-dried silica gel for about 14 days prior to testing in order to improve homogeneity.

Prototypes with designation "PSx" will refer to CO passive samplers of the x-th generation, designed to operate over a 7-day period. Likewise, the prototype designation "Dx" will refer to the 8-hour occupational dosimeter design of the x-th generation. The passive samplers designated PS1 are considered to be the original proof-of-concept design which established the feasibility of the work presented here. Some of the results from the development of the PS1 are included here for completeness.

I. Carbon Monoxide Sensor
A. Sensor Chemistry

The non-regenerating CO sensor type MD15 manufactured by Quantum Group, Inc. responds to CO exposure with a proportional near-linear increase in optical density in the near-infrared region. The chemical formulation of the sensors is described in U.S. Pat. No. 5,733,505 issued on Mar. 31, 1998. The salient features of the chemistry have been discussed in the literature (Goldstein, 1991a; Goldstein, 1991b, Brown 1998). The sensors are made by coating the palladium and molybdenum salts ($PdCl_4$ and $MoO_3$), orange-yellow in color, onto a porous silica-based (VYCOR™, Corning Glass Works, Corning, N.Y., and porous silica substrates, Quantum Group, San Diego, Calif.) circular disk (6 mm in diameter, 1.3 or 2.6 mm thick) with the average pore diameter ranging from 10 to 1000 Angstroms.

B. Mechanism of Sensor Chemistry

A set of possible mechanisms of the sensor chemistry outlined in FIG. 1 was used to develop a model for determining the forward and reverse sensor reaction kinetics. Empirically derived rate constants using this model as a guide are of use in understanding both how the sensor responds to CO and how the response is lost through reversibility as the measured analyte $H_xMoO_3$ (Mo blue) is re-oxidized to $MoO_3$ (Mo(VI)).

C. Procedure for Making QGI-MD Sensors

QGI-MD sensors are covered under U.S. Pat. No. 5,063,164 (Goldstein 1991b), and the general manufacturing process of these sensors is presented in the technical details in that document. However, the following procedures describe the process by which the MD sensors that are used in the LOCD technology are manufactured.

Procedure 1 (MD1 Sensors)

100 pieces of Vycor™ or any porous silica substrates having an average pore diameter ranging from 40 to 500 angstroms are soaked for several days in 15 ml of a pre-mixed solution containing 2.742 mmol of molybdosilisic acid, 6.54 mmol of palladium chloride, 6.545 mmol of calcium chloride dihydrate, and is acidified with hydrochloric acid so that the pH ranges from 0.01 to 2.00 at 20° C. The discs are drained, then oven-dried at 40° C. under ultrapure nitrogen. They are further dried under silica gel for at least 2 weeks before assembling into the samplers.

Procedure 2 (MD15 Sensors)

100 pieces of Vycor™ or any porous silica substrates having an average pore diameter ranging from 40 to 500 angstroms are soaked for several days in a pre-mixed solution containing 2.752 mmol of molybdosilisic acid, 11.2786 mmol of palladium chloride, 4.4625 mmol of calcium chloride dihydrate, 0.3N hydrochloric acid, and 12.335 mmol sulfurous acid with pH ranging from 0.01 to 2.00 at 20° C. The discs are drained, then oven-dried at 40° C under ultra pure nitrogen. They are further dried under silica gel for at least 2 weeks before assembling into the samplers.

D. Theoretical Basis for Measuring Sensor Response

The CO detecting characteristics of the chemistry are based on the oxidation of environmental CO by palladium, which in turn reduces the molybdenum (VI) to a mixed oxidation state species having a blue color ($Mo_{blue}$). This change was shown to be quantifiable by monitoring the sensors' absorbance of light in the visible to near-infrared. In fact, with moderate CO exposure, this change from yellow to blue is visible to the naked eye. The sensors used in the occupational dosimeter have been found to have a peak sensitivity at around 700 manometers (nm).

The spectrophotometric analysis used to assess the sensor response is based upon the Beer-Lambert Law (Peters, 1974), which states that:, for a given wavelength of light energy, $$A = \log\left(\frac{I_0}{I}\right) = \epsilon^{bc} \quad (1)$$

where,

A=Absorbance (A), $I_0$=incident intensity of radiation from a light source onto a sample, I=intensity of light radiation emerging from a sample, $\epsilon$=molar absorptivity of the sample analyte species (mole-$l^{-1}$-$cm^{-1}$), b=path length of the sample (cm), and c=the molar concentration of the analyte species (mole-$l^{-1}$).

In the case of the non-regenerating CO sensors, I and $I_0$ are measurable using a spectrophotometer, and $\epsilon$ may be determined experimentally. (Note: the concentration of molybdenum blue species on the surface of the QGI sensor is the analyte to be measured for quantification of CO exposure). However, the path length (b) and analyte concentration (c) were not easily determined. This was because it was not feasible to measure the quantity and thickness of the coating of the MD-15 sensing material on the porous sensor substrate surface. However, the sensor's response to CO could be measured empirically so it was not necessary to know the true sampling rate or the actual concentration of analyte on the sensor surface. Empirical methods were used to assess the sensor response.

E. Sensor Response to CO

A forward reaction kinetic model of MD-15 sensors are described in literature by Goldstein, 1991a. The literature suggest that the forward reaction presented in steps 1 and 2 of FIG. 1 is a first-order process for CO. This was also evident in the sensor response experiments. Assuming that the production of $Mo_{blue}$ (step 2) is in direct proportion to the concentration of CO, $$d[Mo_{blue}]=k_f[CO]dt. \quad (2a)$$

where $k_f$=overall rate constant for steps 1 and 2:

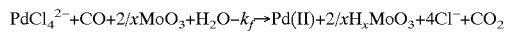

Integrating, $$\int_{[Mo_{blue}]0}^{[Mo_{blue}]}[Mo_{blue}] = \int_0^t k_f[CO]dt. \quad (2b)$$

with [CO] constant. Then, $$[Mo_{blue}]-[Mo_{blue}]_0=k_f[CO]t. \quad (2c)$$

Assuming that the optical density, measured as absorbance of light energy, of the sensor is directly proportional to $[Mo_{blue}]$, i.e., $$[Mo_{blue}]KA, \quad (3)$$

where

K=a sensor-specific constant relating $[Mo_{blue}]$ to the optical density of the sensor (mole-$cm^{-1}A^{-1}$). Then, $$\frac{d[MO_{blue}]}{dt} = K\frac{dA}{dt}, \text{ and} \quad (4)$$

$$\frac{dA}{dt} = \frac{k_f}{K}[CO]. \quad (5a)$$

Finally, the relationship between change in the optical density of the sensor and CO exposure can be described by $$\int_{A_0}^{A} dA = \int_0^t \frac{k_f}{K}[CO]dt \text{ so that} \quad (5b)$$

$$A - A_0 = \frac{k_f}{K}([CO]t). \quad (5c)$$

Note that the quantity [CO]t is the concentration-time product, otherwise termed CO exposure (units=ppm-h). Equation 5c indicates that the change in absorbance of the CO sensors is directly proportional to time-weighted average (TWA) CO exposure. An effective value for $k_f/K$ can be determined empirically and is simply the slope of the linear relationship between change in absorbance of a sensor plotted against CO exposure. The true value of $k_f$ cannot be calculated since K is also unknown. However, an empirical value for the ratio $k_f/K$, henceforth termed k, was derived via a related quantity, the mass-balance relationship between moles (or mass) of CO and dA for a batch of sensors.

$$dA=k[CO]t \quad (5d)$$

describes the empirical relationship between CO exposure and forward sensor response. The units of k are A·$ppm^{-1}hr^{-1}$.

F. Test Method for Assessing Sensor Response

The Direct Method was designed to monitor the CO sensor response to exposure in test atmospheres in near-real-time. This method was very useful for rapid determination of sensor kinetics and calibration curves for the diffusion samplers. Thus, the Direct Method provided a means to quantify and compare sensors' individual responses.

1. Test Set Up

The Direct Method shown in FIGS. 4a, 4b, and 4c used a specially constructed single-sensor (410) flow-through cell (420). It was made from a machined Delrin™ sensor holder (430) fitted into a standard 1 cm spectrophotometric cuvette (440). FIG. 5a and FIG. 5c depict the system for placement of the flow-through cell (510) into the spectrophotometer (520). The Delrin™ and styrene materials were tested for compatibility with the sensor and found to be inert. Small tubes entering (530) and exiting the cell (510) provided for a flow of exposure gases. Operating at a slight positive pressure, the exposure gases were introduced at a flow rate of 10 cc/min. The spehotometer (520) was set to monitor the absorbance of light energy between 400 and 1100 nm. The scan rate of the spectrophotometer (520) was adjusted to a frequency between 6 and 20 scans/h.

2. Test Protocol

A test protocol was developed for the direct exposure method. The flow-through cell, loaded with the non-regenerating MD-15, was placed into the spectrophotometer. The spectrophotometer was started and set to scan automatically at fixed intervals until the end of the experiment. After the first scan, exposure gas supply tubing was connected to the cell inlet. The exposure pattern varied depending upon the objectives of the experiment, but typically the sensor was exposed to a CO environment, usually 40 ppm (±1% supplied from a certified cylinder) for several hours. The selection of 40 ppm was somewhat arbitrary, however this concentration was within in the range of concentrations of the different ambient and occupational air quality standards. (610) shows a typical direct exposure sensor response profile at 700 nm. The sensor absorbance increased with CO exposure. At the completion of the CO exposure period the sensor was returned to storage. Occasionally a sensor's post exposure response was observed in real-time. This was useful for observing the regeneration (reversal) of the sensor response. If the monitoring was continued, the exposure gas supply tubing was quickly (about 1 min.) purged with pure, dry nitrogen or air, and then connected back to the cell. The sensor could be held in a CO-free environment after CO exposure for a period from hours to days in order to monitor any change in absorbance with time; however, since the sensor regeneration occurs over weeks, the method was not practical or assessing sensor reverse kinetics. After removal from the flow-through cell, individual sensors were monitored at various intervals in the spectrophotometer using the Single Scan Sensor Holder (540) shown in FIG. 5d.

3. Results

The sensor response in the visual/near-infrared to CO exposure was assessed by measuring the absorbance spectrum of the sensors in the range of 400 nm to 1100 nm. The exposed sensor coating has strongest absorbance at about 700 nm.

Figure 6:
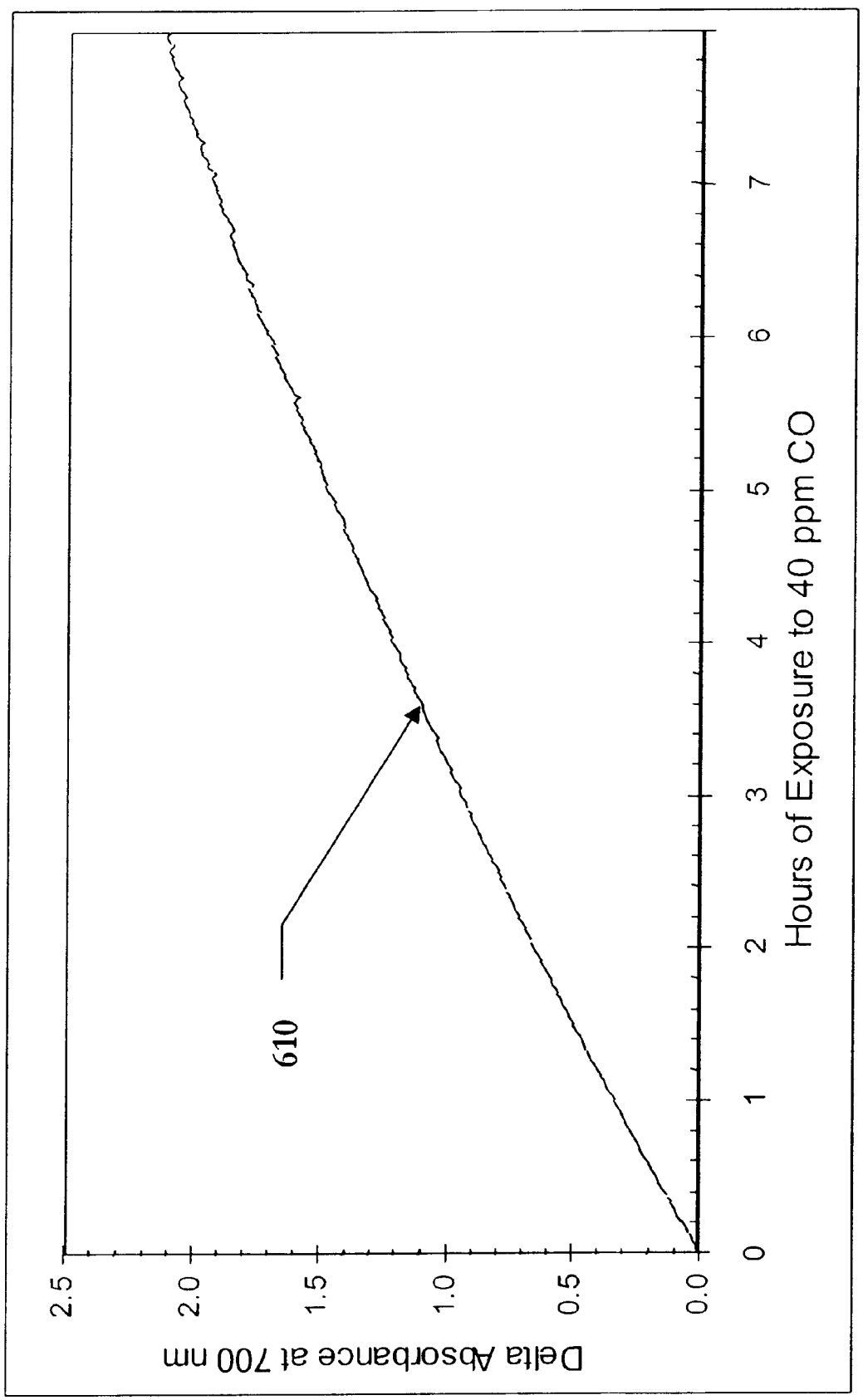
FIG. 6. A typical "direct method" experiment response profile (610) showing the change in absorbance of a sensor vs. duration to 40 ppm CO, measured at 700 nm at 700 nm. Note that CO exposure of the sensor can be calculated by multiplying the time on the x-axis by 40 ppm.

Data collected from the direct method were a series of spectra taken at frequent intervals (2.5 to 10 minutes) for up to 6 or more hours. These data yield real-time response profiles of sensors exposed to a particular concentration of CO. The slope of the response curve (610), in FIG. 6, was proportional to the sensitivity of the sensor and could be used as a calibration curve for the diffusion samplers. The response of typical MD-15 sensors was approximately linear below a dA of about 1.2 A. The sensors' response would start to become non-linear after a dA of about 1.2 was reached. The response was better modeled with a polynomial curve fit after this. For low exposures the linear model was a good approximation which could simplify characterization of the sensors. The apparent non-linearity of response observed (as in FIG. 6) for longer exposures may have been an artifact of the exposure method due to a temporary saturation of the most accessible sensor reaction sites.

Sensor Conditioning Prior to Use

From a practical standpoint, sensors within a batch must be homogeneous in order to manufacture passive samplers with minimum variability. Several factors were found to affect intra-batch sensor homogeneity, but with only one exception, they were all controlled in the manufacturing process. The one exception was the sensor moisture content, the sensors are manufactured with the moisture level at equilibrium with ambient humidity, i.e., at about 50% relative humidity (RH). If sensor moisture content was not controlled, they were found to have a large variability in sensitivity. It was found that when dry, the response characteristics became quite uniform. They were desiccated to equilibrium with fully dried silica gel, a RH very close to zero. It was necessary to desiccate the sensors for a minimum of 14 days to ensure that the sensors were fully dry.

Sensor Testing Results: Inter- and Intra-batch Sensor Variability in Response Slope and Linearity Seven batches of MD-15 sensors were fabricated in order to test the inter-batch and intra-batch variability in sensor response. Table 1 shows the sensor response average of three conditioned sensors each from the 87 batches, AN–AU. It was evident that the inter-batch variability of these sensors was significant. The forward sensor response (k) was calculated for a 4-hour exposure of three sensors to 40 ppm in direct method tests. These data indicated (see $R^2$ values in Table) that, for this section of the response profiles, the sensors' responses were linear. Table 1 presents the slopes (and correlation coefficients) from least-square linear regression fits for each of three sensors for sensor batches AN–AV. The intercepts in these regressions were constrained to the origin, since all sensor exposures started with zero change in absorbance. Note that the slopes of these lines were quite close within batches and, as expected, varied considerably from batch to batch.

An analysis of variance of these data, indicated that the variance in sensor response slopes was due almost entirely to inter-batch differences ($p>0.05$), while no statistical difference ($p<0.001$) could be detected in slopes within batches. When an analysis of variance of the linearity of the sensor response was conducted using the correlation coefficients, the variation in inter-batch linearity explained most of the variance ($p>0.05$), while intra-batch variability was also significant ($p<0.05$). Most of the intra-batch variability in $R^2$ values was caused by the alinearity of one sensor in the AN batch. If the AN batch data are removed from the analysis of variance, the intra-batch variance in sensor linearity was not statistically significant ($p<0.05$).

TABLE 1

MD15 sensor response characteristics.

| Batch | Response of Sensors Within a Batch $k$ ($R^2$) | | | Average ± Std. Dev. |
|---|---|---|---|---|
| | 1 | 2 | 3 | |
| AN | 0.348 (0.999) | 0.333 (0.934) | 0.376 (0.995) | 0.352 ± 0.022 (0.976) |
| AP | 0.308 (0.998) | 0.282 (0.998) | 0.313 (0.997) | 0.301 ± 0.017 (0.998) |
| AQ | 0.273 (0.998) | 0.272 (0.999) | 0.283 (0.999) | 0.276 ± 0.006 (0.999) |
| AR | 0.296 (0.997) | 0.308 (0.996) | 0.302 (0.997) | 0.302 ± 0.006 (0.997) |
| AS | 0.364 (1.000) | 0.359 (0.997) | 0.323 (0.996) | 0.349 ± 0.022 (0.998) |
| AT | 0.381 (0.995) | 0.384 (0.992) | 0.389 (0.996) | 0.385 ± 0.004 (0.995) |
| AU | 0.366 (0.998) | 0.386 (0.997) | 0.368 (0.998) | 0.373 ± 0.011 (0.998) |

Inter- and intra-batch differences.
Sensor response slope (A – hr$^{-1}$) and correlation coefficient from least-squares linear regression.
Forward sensor kinetics were measured using the Direct Method with [CO] = 40 ppm and absorbance measured at 700 nm.

The results showed that, with current QGI manufacturing technology, it was necessary to create a separate calibration curve for each batch of sensors. This was not considered a problem, as calibration curves would be generated for quality control in any case. These data indicate that within batches the sensors were consistent.

4. Sensor Selection

The non-regenerating MD-15 sensor was well suited for use in a passive sampler because 1) its response to CO was sufficiently irreversible; 2) its response was easily measured (optically) without complicated wet-chemical or gas-phase chemistry techniques; and 3) it was small enough to be configured into a very small package requiring no pump or external power. The results from application of the Direct Method described above showed that these sensors performed satisfactorily for incorporation into a diffusion sampler.

II. Diffusive Sampler Technology

A. Description of Passive Sampler/LOCD

The key functional elements of this invention were the application of the non-regeneration CO sensor and the diffusion tube, encased in a sealed housing. A removable plug on the end of the diffusion tube was used to control when the device was able to sample. Desiccant was added to the device so that environmental water would not affect the sensor.

Figures 2A, 2B:
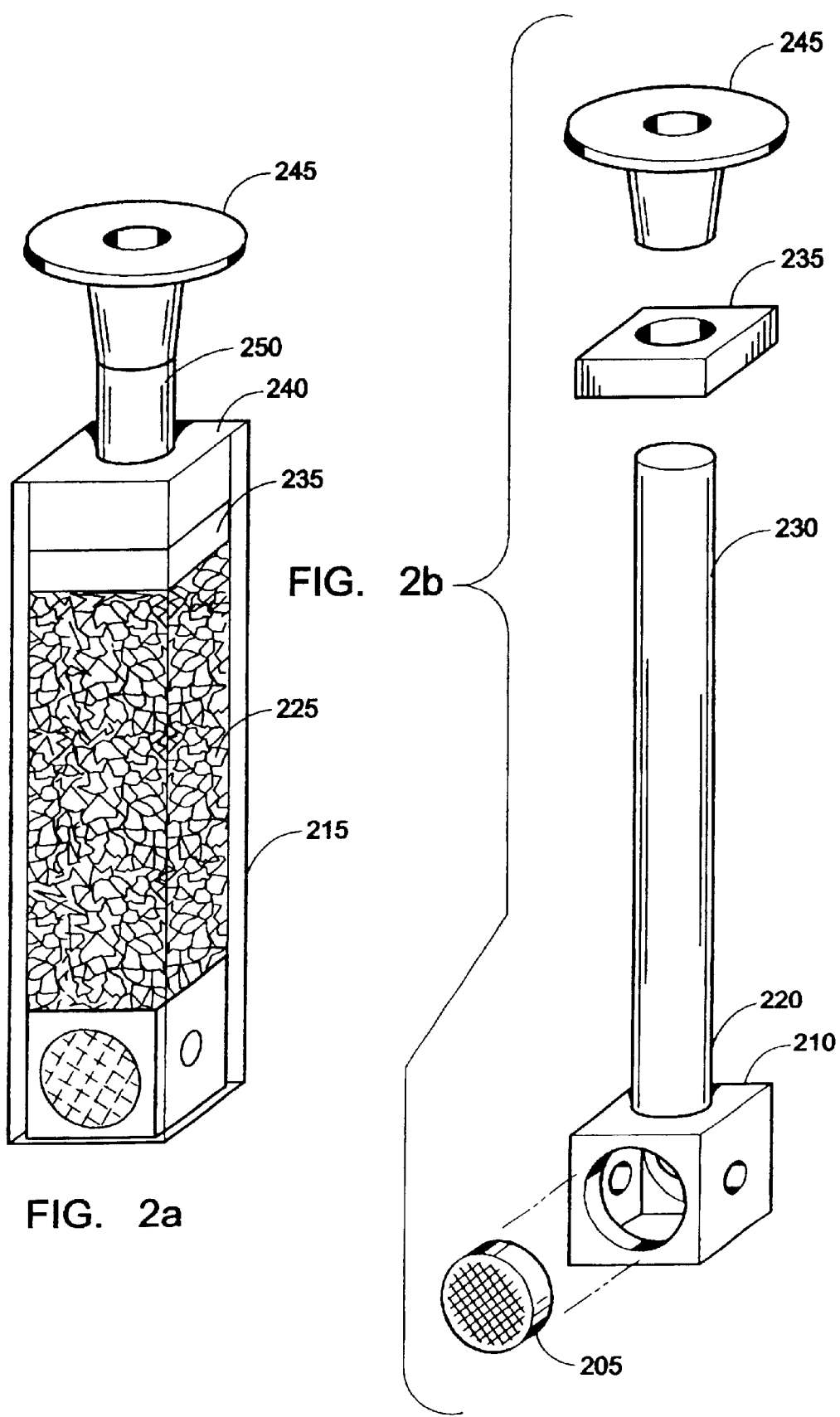
FIGS. 2a and 2b. Schematics of the Occupational Carbon Monoxide Dosimeter and Indoor Air Quality Monitor (LOCD). Not shown is an attachment system comprised of a an integrated chip potted to into the top of the sampler assembly used as a hanger to accept a Snap-On strap with attached lapel clip. This is used for attachment of the device to clothing or subjects for personal sampling, or attachment of the sampler to other objects for area sampling.

The physical description of the present invention is detailed in FIG. 2a and FIG. 2b, and again the engineering drawings shown in FIG. 7. In FIG. 2a and FIG. 2b is a gas-specific sensor (205) intended to respond irreversibly and selectively to the species of interest, located in a specially designed sensor holder (210). A containment system is comprised of a standard 1 centimeter cuvette (215). The sensor holder (210) is especially designed to: a) position the sensor for reproducible measurements within a spectrophotometer; b) accept, position, and retain the internal end of the diffusion tube (220); and c) allow for transfer of interfering species to sorbent materials (225) placed above the holder (210). A diffusion sampling system is comprised of a tubing (220) with dimensions specified to fall within tolerances acceptable to maintain low inter-sampler variation in gas mass transfer rate according to Fick's Law. Element (225) is a gas-phase interferent scrubbing or conditioning system typically used for controlling humidity, comprised of a charge of sorbent material such as indicator silica gel, placed in the cavity above the sensor holder. Element (235) is specially engineered gas-tight fitting which seals tightly against the inside walls cuvette, positioning approximately 0.5 cm from the opened end, and also centers and seals the diffusion tube which penetrates through the center. Element (240) is an epoxy potting material used to make the final seal and adhesive filling the top 0.5 cm of the cuvette. Element (245) is a low density polyethylene plug used to plug the outer end of the diffusion tube (250). The plug (245) controls the time and duration of sampler deployment. Removing this plug (245) will initiate sampling while recapping will conclude sampling. Not shown in FIG. 2a is an attachment system comprised of a an integrated clip potted into the top of the sampler assembly used as a hanger to accept a Snap-On strap with attached lapel clip. This is used for attachment of the device to clothing or subjects for personal sampling, or attachment of the sampler to other objects for area sampling.

Bar Coding

For exposure monitoring studies where a sample size of 100 or more is required, a bar coding label can placed on each dosimeter, avoiding covering the optical windows on either side of the sensor. The bar code can be read automatically by a bar code reader and sample identification data can be logged into a computer or laboratory information system as the dosimeter is placed into the spectrophotometer for absorbance measurements. This data collection enhancement improves the dosimeter system by making the process of sample tracking more reliable and reduces the amount of labor involved in data analysis. It is recommended that a spectrophotometer be available for at the workplace for quick turnaround of dosimeter analysis and results.

Photon Detection System: An Inexpensive Alternative to a Spectrophotometer

A spectrophotometer can be replaced with an alternative, inexpensive photon detection system (PDS). This system consists of a light emitting diode (LED) or a laser diode (for increased signal to noise ratio), a photodiode, and temperature compensated analog signal processing circuitry. A computer or other data collection device is used to store sensor response of the detector. This PDS passes light energy normal to the dosimeter side, into the first optical window of the dosimeter, the pollutant specific sensor (i.e., QGI-MD15 CO sensor), exiting out of the second optical window, finally arriving at the surface of the photodiode for detection. For the MD15 CO sensor, the spectral range usable of usable LEDs for this system is between about 650 nm to 1100 nm, with an optimum of 700 nm. This system measures the change in voltage of the photodiode which can be converted into a measurement of optical transmittance as the optical density of the sensor changes with exposure.

A more sensitive and accurate PDS can be designed incorporating a split-beam or dual-light-source dual beam system. Here, one beam is used unobstructed as a reference, while the second accepts the dosimeter with sensor perpendicular to its path. Each beam has a one of a pre-matched pair of photodiodes or other appropriate photodetector. The baseline optics are nulled in the condition where no obstruction exists in the sample beam path. Measurement of the optical density of a sensor is conducted by placing the dosimeter sensor into the sensor beam path; the transmittance (T) of energy through the sensor is defined as the ratio of the null-adjusted voltage output of the sample beam detector (I) to the reference beam detector ($I_0$). The absorbance (A) of the sensor is defined as in Equation 1.

A working PDS must be designed to shield the optical system from ambient light, and have a dosimeter holder design that ensures reproducible placement and orientation of dosimeters with respect to the light path. The PDS must have a photometric range from 0.000 to 4.000 A, with a photometric accuracy of 0.005 A and precision of 0.001 A. Its linearity should be ±1% throughout its photometric range.

B. Theoretical Basis of Diffusive Sampling

The diffusion sampling approach was selected because well-established methodology exists, based by Fick's law of diffusion (Palmes, 1976; Rose, 1982), to collect time-averaged gas samples inexpensively.

An advantage of the diffusion sampler design was that sampling rates (and sampler capacity) could be varied with a simple change of the diffusion tube dimensions. Mathematically, given the assumption that the sensor has 100% collection efficiency, Fick's Law can be stated by the following equation.

$$M = \frac{D_{CO}CAt}{L} \qquad (6)$$

where:

M=mass diffused to end of diffusion tube ($\mu$g);

$D_{CO}$=diffusion coefficient for CO in air (0.245 cm$^2$/sec);

C=bulk air to sensor surface CO concentration gradient where the CO concentration at the sensor is assumed to be zero; i.e., ambient concentration of CO at tube entrance ($\mu$g/m$^3$);

$A_x$=cross-sectional area of tube (cm$^2$);

t=sampling time (sec);

and

L=length of tube (cm).

C. Sensor/Diffusive Sampler Integration

This relationship defines the parameters needed to engineer a diffusion sampler for a given application. Thus, within the limits of the rate at which the sensor interacts with CO, using a shorter tube, or one with a larger inside diameter will lead to a greater diffusion sampling rate. An optimum range of sensor response could be achieved by properly designing the sampler geometry. It was possible to configure a passive sampler to collect for 168 hours (1 week) or an occupational dosimeter to collect for 8 hours, in part, by changing the diffusion tube. The initial design for the passive sampler used a configuration suitable for 168-hour sampling. Rearranging equation 6, and converting the time units from seconds to hours, an expression for the theoretical mass conversion rate of the diffusion samplers can be derived:

$$q = \frac{3600\, M}{Ct} = \frac{3600 D_{CO} A_x}{L}, \qquad (7)$$

where q=the diffusion sampler's mass conversion rate ($\mu$g-ppm$^{-1}$hr$^{-1}$).

This rate represents the as of CO that is involved in the initial CO—Pd reaction shown in FIG. 3, Step 1a. Note that the sampling rate of the diffusion sampler is dependent upon the CO concentration gradient between the bulk-air and the sensor surface. Also note that the actual sampling rate of this diffusion sampler cannot be directly calculated because of the nature of the MD-15 sensor, i.e., the exact relationship between dA and the mass, M, of CO reacted with the sensor is unknown.

D. Diffusive Sampler Test Method

1. Test Set Up

The propose of the diffusion sampler laboratory exposure method was to test the performance of passive diffusion sampler configurations, in contrast to the Direct Method that was developed to test individual sensors. It was a test regime where samples were exposed to CO, and possibly other gases, under controlled conditions. Prototype passive samplers were exposed to test atmospheres, in a temperature and humidity controlled environmental chamber made of a 3-liter gas reaction vessel. FIG. 8 depicts the diffusion sampler exposure test setup. The instruments used in this setup are listed in Table 2.

Ports on the reaction vessel were connected to the laboratory gas flow system so that an atmosphere of exposure gas could be created. A typical flow rate for the system was 1.0 l min$^{-1}$. The pressure of the exposure chamber was maintained slightly above atmospheric pressure (200 Pa). CO concentration and humidity were measured downstream of the exposure chamber. All environmental parameters under control, including CO concentration, were recorded by the data acquisition system. Typically, for the diffusion method experiments, 10-minute averages of the monitored parameters were recorded.

2. Measurement of Sensor Absorbance

The change in optical density of the sensors caused by CO exposure was quantified by measuring the change in the sensor's absorbance (dA) of light (400 to 1100 nm) before and after exposure. The 700 nm measurements were used for analysis. The sensors were placed individually in the single-scan holder (540) in the spectrophotometer (520) as shown in FIG. 5a and FIG. 5d. The spectrophotometer sample chamber (550) was purged with ultra-pure air to prevent sensor contamination from ambient air. The sensor absorbance spectrum was scanned four times for each measurement. The sensor orientation was changed for each scan, and the four scans were averaged. Post-exposure changes in absorbance due to sensor regeneration were also measured using this method.

TABLE 2

Instrumentation used for laboratory testing of the QGI CO sensors and the LBNL/QGI Passive Sampler and Occupational Dosimeter prototypes.

| Function | Device | Specifications | Manufacturer/Model |
|---|---|---|---|
| Pure air generation (805) | Catalytic pure air generator | Output: 0–20 lpm, Hydrocarbons < 5 ppb, CO < 5 ppb, Dewpoint < −60° C. | AADCO model 737 |
| Gas flow control (810) | Mass flow controller | Range: 0–200 sccm, 0–2 slm, 0–20 slm Accuracy: ±1% | Brooks/5800 series Matheson/FC200 |
| Gas mixing (815) | Glass gas mixing manifolds | 2 to 1 and 6 to 1 multi-ported glass manifolds | LBNL Glass Shop |
| Thermal exposure control (820) | Temperature controller water bath | Temperature range: 0–100° C. | Forma-Scientific Model 2067 |
| Humidity generation (825) | Fritted glass bubblers in gas wash bottle. | Two glass gas wash bottles with fritted bubblers. Splitter valve used to adjust amount of water vapor flowing into exposure stream. | LBNL |
| Exposure chamber (830) | Glass reaction vessel | 3 liter glass reaction vessel with clamped ground glass cover flange. Stainless steel cover plate with 10 threaded ports | ACE Glass Co. LBNL |
| Data acquisition | 16 channel data acquisition system | 12 bit, 16 channels, RS-232 interface to PC. LBNL SAM software. | LBNL/Fawlkes Engineering |
| Temperature (835) | Sealed, waterproof AD590 temperature probes | Range: 0–100° C. Accuracy: ±0.2° C. | Analog Devices/AD590 LBNL packaging and calibration. |
| Humidity | Chilled Mirror Dewpoint Hygrometer | Range: 0–50° C. Accuracy ±1° C. | General Eastern/DEW10 |
| Pressure (840) | Magnehelic pressure gauge | Range: 0–2000 Pa Accuracy: ±50 Pa | Dwyer/2008c |
| CO concentration (845) | Gas filter correlation infrared analyzer | Range: 0–1000 ppm CO Accuracy: ±1% | Thermo Environmental/48 |
| Spectral absorbance | UV-Near infrared spectrophotometer | Spectral range 180–1100 nm Absorbance range 0.001–6.000 A Accuracy: ±0.005 A | Perkin Elmer/Lambda 2 |

3. Test Protocol

The following test protocol was developed so that different sampler configurations could be compared: Sensors were desiccated for at least two weeks prior to exposure (this desiccation period was found to be an important factor in controlling sensor response rate, as discussed above). A pre-exposure measurement of sensor absorbance spectra were taken. Samplers were assembled using the sensors to be tested. Two or more samplers, left unexposed, were used as controls. They were handled identically to the test samplers and were measured with each measurement of the exposed sensors. Various CO concentrations of between 5 and 100 ppm were used in the exposure chamber depending upon the experiment. After exposure, the samplers were removed from the exposure chamber, disassembled, and measured in the spectrophotometer.

Typically a series of exposures were conducted on a set of samplers with sensor absorbances measured before and after each exposure. For example, in some experiments the PSx samplers were removed from the exposure chamber and measured once every 24 hours for one week. The Dx prototype occupational dosimeters were typically exposed to CO in a sequence of four 4-hour periods. Delta absorbance values were calculated by subtracting the initial absorbance prior to the first exposure from the absorbances after the subsequent CO exposures. These dA values were plotted against their cumulative CO exposures.

4. Data Collection

Data collected using the diffusion sampler exposure method yielded a pair of data points at 700 nm for each exposure to CO. This was because the absorbance spectra were only measured prior to and after exposure. The change in absorbance (or the difference in absorbance between these two points) with exposure to CO, for a sensor exposed in a diffusion sampler, were used to compute the CO exposure of the sampler.

D. Empirical Calibration Factor

An empirical calibration based on data collected from both the direct tests and a series of laboratory diffusion exposure tests at a range of exposures were made in order to compare the passive sampler response to the response characteristics of sensors from the same batch. Once this relationship was determined it was possible to superimpose the direct test response curves onto plots of delta absorbance data collected from diffusion samplers in a sequence of controlled CO exposures. The diffusion samplers were calibrated for each batch of sensors to remove the variability caused by inter-batch differences in sensor response. This calibration accounted for the increased restriction in the diffusion path created by the diffusion tube. The assumption was that the rate at which CO molecules diffused to the sensor in the direct tests was a constant. Given this assumption it was possible to scale the response of the passive samplers relative to that of the sensors tested using the Direct Method. Normalizing to the direct exposure regime, the ratio of the response of the sensor in the sampler to what it would have been in a direct test should be a constant. This relationship will be called the diffusion scaling factor, R, calculated as follows:

$$R = \frac{e}{e_{eff}} \quad (8)$$

and $$e_{eff} = \frac{dA}{k} \quad (9)$$

where,

R=the diffusion scaling factor (unitless),
$e_{eff}$=effective exposure of sensor (ppm-h),
e=actual exposure of sampler (ppm-h),
dA=delta absorbance of sensor (A),
and
or k=derived forward response (slope) of sensor batch from direct tests (see Equation 5d, A-ppm$^{-1}$h$^{-1}$).

The empirically derived diffusion scaling factor was useful for comparing the observed sensor response under the direct and diffusion sampling modes, two very different exposure regimes.

The Diffusion Sampler Laboratory Test Method produced a sequence of two or more absorbance measurements related to CO exposures. These dA values were plotted against their respective exposure levels, e in ppm-h. In the simple case, where samplers were only exposed once, the sample response was merely dA/e. However, when a set of samplers were exposed to a sequence of exposure regimes and corresponding change in absorbances were measured, the slope of the line fitted (using a least-squares linear regression) through these points was calculated. This slope, $$\rho = \frac{dA}{e}, \quad (10)$$

was the average response of the samplers for these exposure regimes. Once calculated for a batch of samplers ρ was used as a calibration to calculate the exposure of samplers. From Equation 10, $$e_{calc} = \frac{dA_{sampleer}}{\rho}, \quad (11)$$

where:

$e_{calc}$=the calculated TWA exposure of the sampler (ppm-h), and
$dA_{sampler}$=the measured pre and post exposure difference in sensor absorbance at 700 nm (A).

Note that e is the actual exposure whereas $e_{calc}$ is the measured exposure calculated from the change in absorbance of the CO sensor.

III. Reference Standards for Comparing Diffusive Sampler Performance

Precision, bias, and accuracy have formal definitions set forth by NIOSH with regard to air sampling analytical method development (Kennedy, 1995). In this work they are only used to discuss the results of the fully functional occupational dosimeter. In other instances test results are presented in terms of sample mean, standard deviation, and relative standard deviation.

NIOSH defines precision as the "relative variability of measurements on replicate samples about the mean of the population measurements." In reality this is merely the relative standard deviation, the standard deviation of a set of individual measurements divided by their mean (Kennedy, 1995).

Bias is defined as the "uncorrectable relative discrepancy between the mean of the distribution of measurements from a method and the true concentration being measured, T as expressed as a fraction. It is given by B=[(μ/T)−1]." In the context of this work T is the true CO exposure as measured by the calibrated CO analyzer and μ is the mean of measured values (e) of a set of exposed dosimeters (Kennedy, 1995).

The definition of accuracy set forth by NIOSH is "the ability of a method to determine the "true" concentration in the environment sampled. The accuracy of a method is the theoretical maximum error of a measurement, expressed as the proportion or percentage of the amount being measured without regard for the direction of the error, that is achieved with 0.95 probability of the method." NIOSH provides a method for the calculation of accuracy based upon measured bias and precision from experimental data. A nomogram providing hyperbolic curves relating bias and precision to accuracy is provided in Kennedy, 1995. The accuracy calculations for sets of dosimeters presented in the dosimeter performance results section was simplified using this procedure.

IV. Diffusive Sampler Designs

A. PS1 Design

Figure 9:
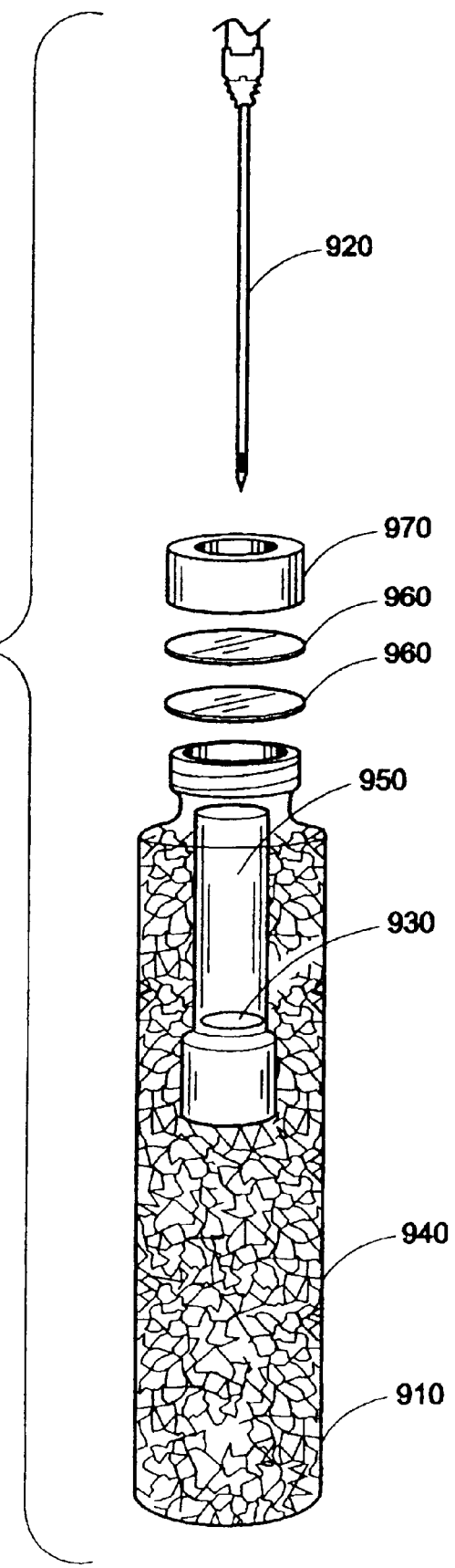
FIG. 9. Diagram of the first prototype LBNL/QGI passive sampler (PS1).

The design of the first prototype CO passive sampler (PS1) is depitted in FIG. 9. The key points of the design were a) a large excess of dry silica gel (910) to adsorb any water vapor in the sample stream, and b) a well defined sampling rate based on Fick's Law and the geometry of the diffusion tube (920) and sensor (930). The sampler body was a glass vial (940). The vial was filled with indicator silica gel (910). A porous polyethylene tube (950) (Porex Technologies, Fairburn, Ga.) with the non generation sensor MD-15 (930) placed at the lower end was embedded into the silica gel (910) in the vial. A silicon rubber and PTFE septum (960) was placed in an open-faced cap (970) at the top of the vial (940). A 16 gauge hypodermic needle (920) was inserted into the septum protruding down into the void space inside the porous internal tube. The needle acted as a diffusion tube, fixing the sampling rate of the sampler. The porous tubing (950) allowed moisture to diffuse out of the sampling path before reaching the sensor. The silica gel (910) acted to keep the entire system dry.

Figures 10A, 10B:
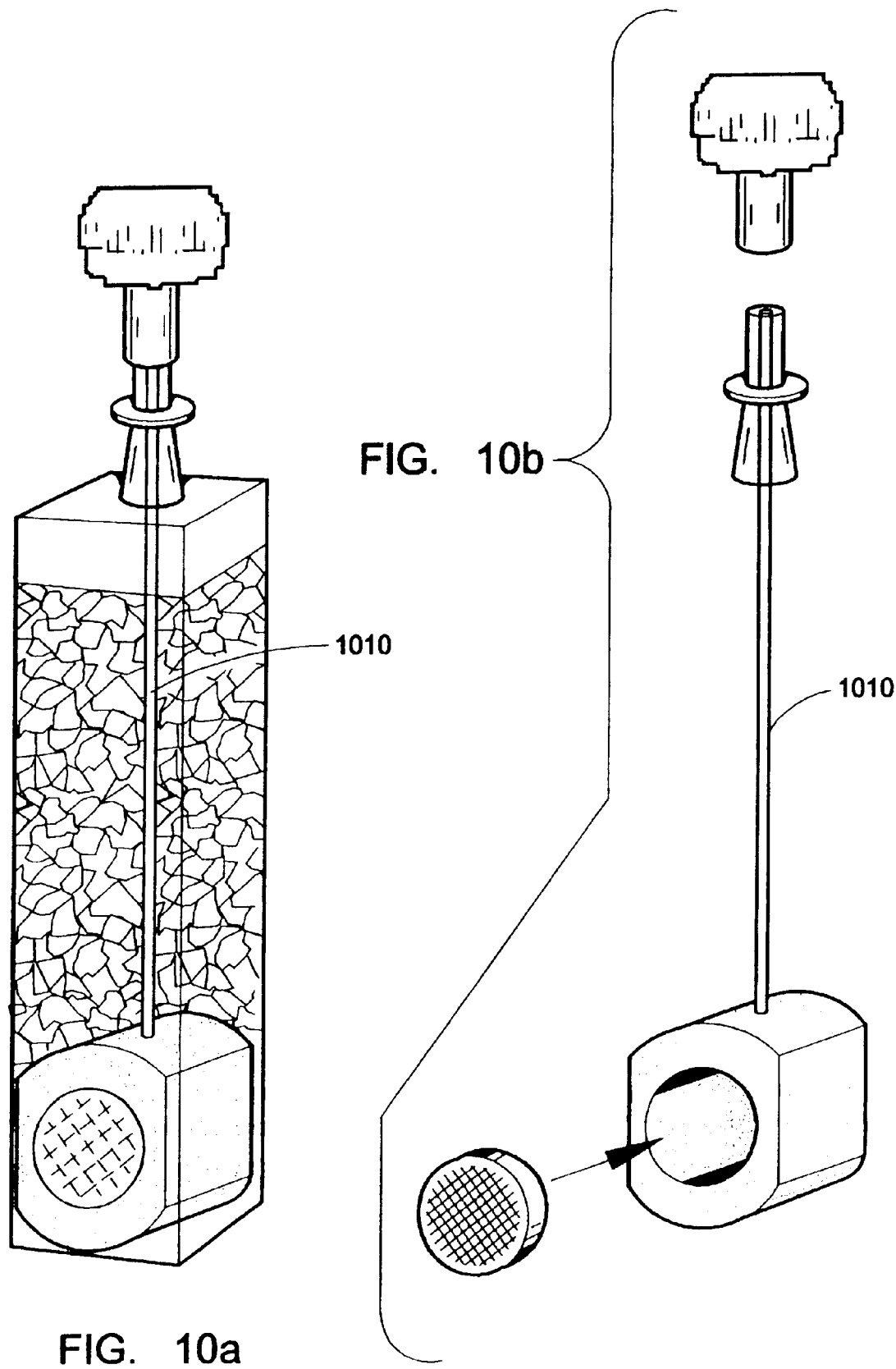
FIGS. 10a and 10b. Schematics of the LBNL/QGI Passive Sampler #2 (PS2).

PS1's laboratory test results proved the CO passive sampler concept, however the device was not practical for use in large scale field tests. Analysis was very cumbersome because it was necessary to disassemble the samplers in order to remove the sensors. The samplers were prone to leakage around the cap and at the needle hole in the septa. The glass body and the hypodermic needle were unsuited for use in field studies where improper handling could lead to an injury of a participant. These issues were dealt with in subsequent prototypes. B. PS2 Design An improved CO passive sampler prototype, the PS2, suitable for use as an occupational dosimeter, was designed and constructed (see FIG. 10a) to improve the design to 1) miniaturize and reduce weight; 2) reduce blank exposure (e.g., reduce leaks); 3) improve the safety of the design for field use (e.g., remove hazardous components); 4) improve sample analysis methodology; and 5) improve, precision and reduce inter-sampler variability. It was also necessary to re-configure the diffusion tube (1010) dimensions for use as an 8-hour dosimeter. The 8-hour design is referred to here as the PS3 which was the same as D1, the fist occupational dosimeter.

1. Advantages of PS2 Over PS1

The PS2 had several advantages over the original prototype PS1, achieving most of the goals listed above. However, its underlying principle of operation was identical to that of its predecessor. The PS2 design was small and compact, and CO exposure could be measured directly. It was rectangular in shape (1.3 cm×1.3 cm×4.5 cm) and was well suited for use in mail out studies, or to be worn as a personal sampler.

The PS2 design was intrinsically safer than its predecessor. The hypodermic needle previously used for a diffusion tube was replaced with a 4 cm piece of 1 mm outside diameter (OD, 0.5 mm inside diameter [ID]) PTFE, or 15.6 mm OD (4.8 mm ID) brass tubing for the one-week passive sampler and the 8-hour dosimeter, respectively. The diffusion tubes fixed into place and the cuvette was sealed with epoxy sealant. The glass vial was replaced with a plastic (styrene) cuvette. The new prototype design required less desiccant than PS1. Based on calculations of the actual amount of silica gel needed, this amount was reduced significantly. The entire unit was permanently sealed so it could no longer be disassembled. With these improvements the samplers were essentially tamper-proof, ensuring that they would be safe for deployment in the field.

The PS2 design allowed for ease of analysis. The device was built into a standard spectrophotometric cuvette. With these improvements pre and post-exposure measurements could be made without disassembling the passive sampler. In FIG. 5a and FIG. 5b, the "Dosimeter Holder" (660) shows how the $PS_x$ and $D_x$ samplers were placed in the spectrophotometer. As described it FIG. 1. And FIG. 5, the sensor was permanently positioned within the cuvette so that when placed in a spectrophotometer (520) it was automatically sealed in the optical path of the measurement beam. Analysis was accomplished simply by placing the sampler into the standard cuvette holder of a spectrophotometer (see Dosimeter Holder (560) in FIG. 5). Another benefit of the design was that the sensor position within the sampler was fixed. Because the orientation of the sensor with respect to the spectrophotometer beam could not change between subsequent measurements, measurement precision was improved. The height adjustment on the dosimeter holder (560) was positioned so that the light beam would be centered on the CO sampler sensors.

2. Material Selection

All of the materials considered in the manufacturing of PS2 including the sensor holder, adhesives, and sealants were tested for compatibility to eliminate any possibilities that the sensors performance might be affected by high concentrations of plasticizers and certain volatile organic compounds, see Table 3. Only those materials which were found be compatible with the sensors were used to build PS2.

TABLE 3

Materials compatibility tests for LBNL/QGI carbon monoxide passive samplers.

| Material/Test Condition | Function in sampler | Results | Difference relative to control* | Comments |
| --- | --- | --- | --- | --- |
| Styrene | Sampler body. styrene disposable cuvette | Non-interfering | −10 ± 40% | Melted styrene caused interference |
| Porex ™ | | | | |
| Aged: | Diffusive sensor holder | Interfering | −40 ± 40% | Cleaned in ethanol and baked at 40° C. for 24–48 hours |
| New: | | Interfering | 40% | |
| Baked 24 h: | | Interfering | 40 ± 10% | |
| Baked 48 h: | | Non-interfering | 2 ± 2% | |
| Neoprene | Seal | Interfering | 60 ± 20% | |
| Sealing wax | Sealant | Interfering | 120 ± 20% | Interfering with and without addition of cuvette |
| Hot melt glue | | | | |
| Low Temp: | Sealant | Interfering | 500 ± 60% | Both low/high temperature settings |
| High Temp: | | Interfering | 600 ± 40% | |
| Melted paraffin wax | Sealant | Interfering | −20 ± 30% | Appeared to interact with epoxy |
| Water-based putty | Sealant | Interfering | −80 ± 40% | Possible negative interference with water released during curing |
| Epoxy Sealant | | | | |
| Epoxy only: | Sealant | Non-interfering | 3 ± 9% | Low viscosity |

TABLE 3-continued

Materials compatibility tests for LBNL/QGI carbon monoxide passive samplers.

| Material/Test Condition | Function in sampler | Results | Difference relative to control* | Comments |
|---|---|---|---|---|
| Wax layer: | | Interfering | 30 ± 30% | potting system. Less interference without paraffin wax layer. |
| Silica gel | Desiccant | Non-interfering | NA | Baked out at 110° C. for 24 hours. |
| Teflon | Diffusion tube and support | Non-interfering | NA | Cleared in ethanol and baked out at 40° C. for 24 hours |
| Nylon | Inlet fittings and plugs | Non-interfering | NA | Cleaned and baked out at 40° C. for 24 hours |

*Mean percent difference (± relative standard deviation) in delta absorbance between sensors exposed to materials and sensors stored in identical conditions without materials (controls).
A difference of 10% in absorbance from the control value indicates an incompatible material.

C. PS3/D1 Designs

After testing PS2 with a diffusion tube diameter (1 mm) and length (4 cm) similar to that of PS1, a small number of samplers (referred to as PS3 or dosimeter 1, D1) were constructed using inlet diffusion tubes with larger diameter (4.8 mm ID×4 cm, 5.6 mm OD) to allow more CO mass to diffuse to the sensor in an 8-hour period, as required for occupational dosimetry.

D. D2 Design

The second dosimeter design D2 is shown in FIG. 2a and FIG. 2b. A new sensor holder (210) was designed to increase the water vapor transfer rate to the silica gel and improve the manufacturability of the device. This holder was made of a machined black polycarbonate cube, a plastic material that had been tested for compatibility with the non-regeneration carbon monoxide sensor. The holder contains numerous small ports on all faces except the two perpendicular to the optical path which hold the sensor. Additionally, the vertical sides of the cube were slotted to allow water vapor to diffuse up from the bottom of the cuvette into the silica gel. The sensor holder (210) was machined to fine tolerances so that 1) it fit perfectly into the plastic cuvette and 2) the diffusion tube (230) would snap into it. FIG. 2 also shows the new seal (235) that was designed to align perfectly and seal against the diffusion tube and the mating surfaces of the cuvette walls. The seal (235) was also machined from black polycarbonate plastic. The sealing edges were cut at 12° in order to make a tight closure.

In order to test the response and humidity control performance of the newly designed D2, a preliminary batch of 20 pairs of sensor holders and seals were manufactured. These parts were assembled into dosimeters using 40.6±0.05 mm (1.6 inch) lengths of 5.6 mm OD (i.e., nominal 7/32 inch OD, ID=4.8 mm brass tubing, and pre-conditioned 7-20 mesh indicator silica gel, lightly packed into the dosimeter cavity.

The primary functional change implemented in the design of D2 was the increased water vapor transfer capability of the machined sensor holder. It was necessary to test the performance of the dosimeters with this improvement. Test result is presented below.

D. D3 Design

Once the design improvements of the D2 sampler were verified a large batch of dosimeter parts (about 400 sets) were manufactured. These parts were very similar to the small batch of 20 sets used in D2, with the exception that dimensions in the sensor holder were slightly changed. Due to the fact that these samplers were mass produced and because of the small design changes this version of the occupational dosimeter (now model D3) was named the "LOCD", an acronym for LBNL/QGI Occupational CO Dosimeter.

V. Laboratory Test Results

A. PS2 Test Results

Figure 11:
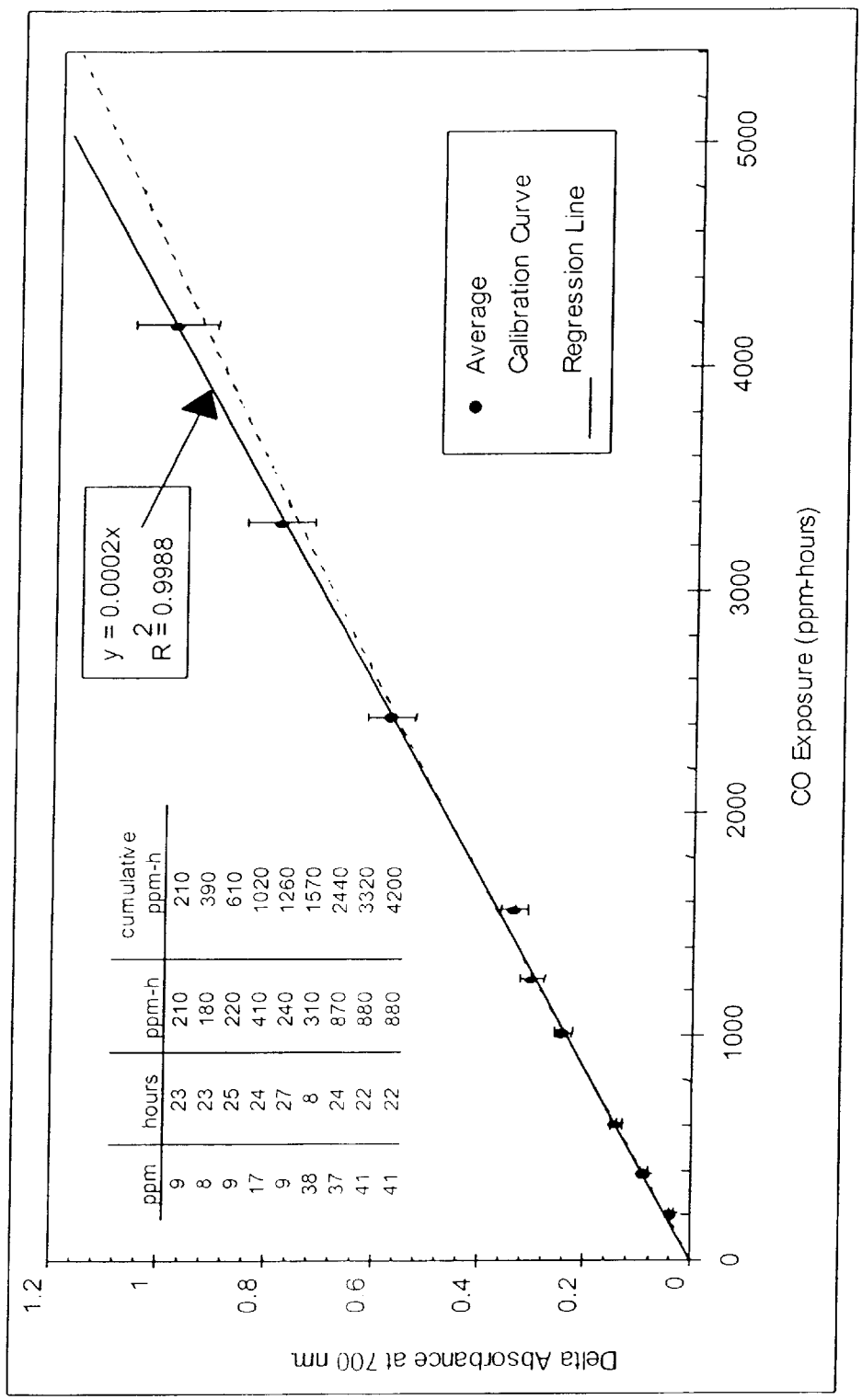
FIG. 11. LBNL/QGI PS2 passive sampler laboratory test results. Five PS2 were exposed to CO from 200 to 4000 ppm-hours in dry conditions. The dashed line (1120) indicates the sensor calibration curve derived from direct method tests. The solid line (1130) is a least-square regression fit to the average sampler response. The CO exposure data are presented in order in the superimposed table (1110). Note that exposure concentrations ranged from 8 to 41 ppm.

Groups of five PS2 samplers configured for 1-week sampling were exposed in the laboratory under dry conditions using the diffusion sampler test method described above. The exposure ranged from 180 to 4200 ppm-hours, at concentrations from 8 to 41 ppm and the exposure duration ranged from 8 to 168 hours. The response of the samplers is shown in FIG. 11. The concentration-duration of CO of each consecutive exposure is tabulated (1110) on the FIG. 11. The error bars on the data points in FIG. 11 represent ±1 standard deviation, an indication of the spread in response of five samplers at a given exposure level. The dashed curve (1120) superimposed on FIG. 11 is the scaled Direct Method response curve for the batch of sensors used. The solid line (1130) through the points is a least-square regression fit of the data, indicating a sampler response, ρ, of 0.0002 A-ppm$^{-1}$hr$^{-1}$. The response of these samplers was very linear ($R^2$=0.999), with an average RSD of 8.5% across the range of exposures. The lowest exposure level was about 200 ppm-h, equivalent to about a 1.2 ppm average for a week. The RSD of the 5 sampler measurement was 13.6% for this exposure level. On the other extreme, the samplers were exposed to the equivalent of 25 ppm for a week (4200 ppm-h) with an RSD of 7.8%. At the highest exposure level the maximum average change in absorbance was less than 1A. Direct method measurements indicated that the sensor response range goes up to a change in absorbance of about 3A. Although never tested to their limit, the PS2 should be capable of measuring a one-week average exposure of up to about 75 ppm, or 13,000 ppm-h.

The average diffusion scaling actor, R, for the PS2 across the exposure range was 33.8 (RSD=5.0%). This is a function of the sensor kinetics and geometry of the diffusion tube configuration. With a change in sampler configuration, the range of the sampler was extendible either for use in different concentration ranges or sampling duration. The low variability in R for this sampler configuration indicates that the sampling rate was fairly uniform across a wide range of exposures.

The linearity of the sampler response when they were exposed to a range of concentrations indicated that they appear to perform independent of concentration in the range of 8 to 40 ppm. The sixth exposure point (1140) on the response curve, 8-hr×38 ppm in FIG. 11, fell slightly below both the line of best fit and the superimposed scaled direct exposure trend. This was the only exposure datum to diverge from the expected response. It was also an 8-hour exposure, a duration about one-third or less as long as the others in the test. It is possible that the observed reduced response was due to the shorter exposure duration. Recall that the PS2 samplers were configured to sample for up to one-week or more. The observed underestimate of exposure for the 8-hour exposure may indicate that the performance of the PS2 may be compromised if a sampling duration of 20-hours or less is used.

The average diffusion scaling factor, R, for the PS2 across the exposure range was 33.8 (RSD=5.0%). This is a function of the sensor kinetics and geometry of the diffusion tube configuration. With a change in sampler configuration, the range of the sampler was extendible either for use in different concentration ranges or sampling duration. The low variability in R for this sampler configuration indicates that the sampling rate was fairly uniform across a wide range of exposures.

The linearity of the sampler response when they were exposed to a range of concentrations indicated that they appear to perform independent of concentration in the range of 8 to 40 ppm. The sixth exposure point on the response curve (8-hr×38 ppm, see FIG. 9) fell slightly below both the line of best fit and the superimposed scaled direct exposure trend. This was the only exposure datum to diverge from the expected response. It was also an 8-hour exposure, a duration about one-third or less as long as the others in the test. It is possible that the observed reduced response was due to the shorter exposure duration. Recall that the PS2 samplers were configured to sample for up to one-week or more. The observed underestimate of exposure for the 8-hour exposure may indicate that the performance of the PS2 may be compromised if a sampling duration of 20-hours or less is used.

B. PS2 Test Controls

Figure 12:
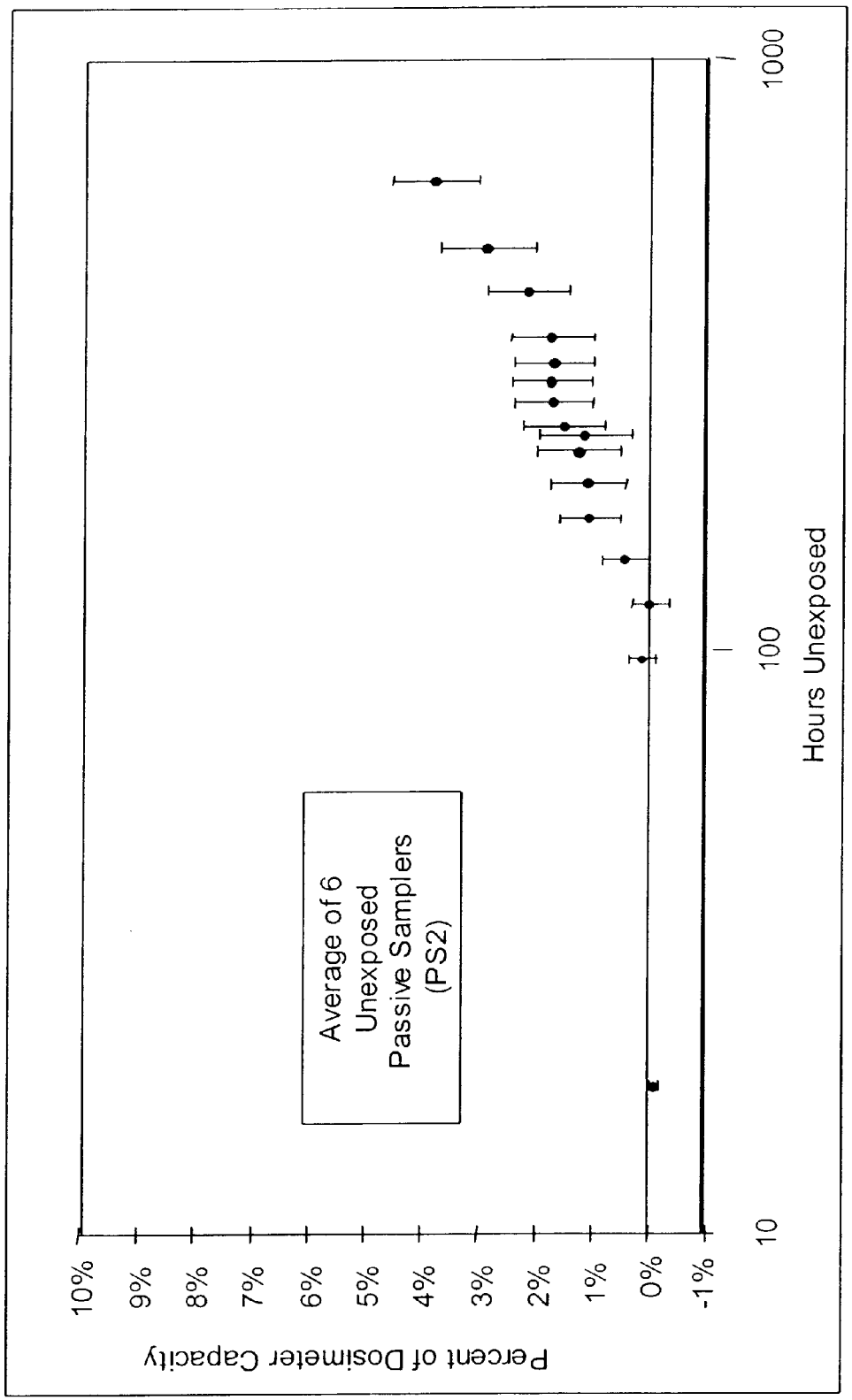
FIG. 12. Average increase in background absorbance of six capped PS2 LBNL/QGI CO passive samplers exposed to CO environments as controls over more than 600 hours. Error bars represent 1 standard deviation.

Unexposed PS2 samplers, used as controls with a group of exposed samples, are necessary to account accurately for any background changes in sensor absorbance. The use of laboratory and field controls is standard for any pollution measurement surveys involving samplers. The most likely cause of absorbance in unexposed samplers is air leakage. The design of PS1 was quite leaky. The use of the epoxy potting material as a sealant in PS2 reduced this leakage significantly, however some background increase in absorbance was still noticeable in these samplers. FIG. 12 shows the response of passive sampler controls which remained capped, but were placed in 8 to 40 ppm CO environments for more than 650 hours. Although this background drift was quite small, possibly some of the increase was caused by a response to one or more components of the materials that were present. Small leaks the PS2 sampler were likely the main cause of the sensor response. The sampler response is shown as a function of a nominal sensor capacity (dA of 2.5 A). The average change in absorbance was about 0.1 A over the 650 hour period corresponding to an equivalent CO exposure of 500 ppm-h (or 0.8 ppm average over the 650 hours).

C. PS3/D1 Laboratory Test

Figure 13:
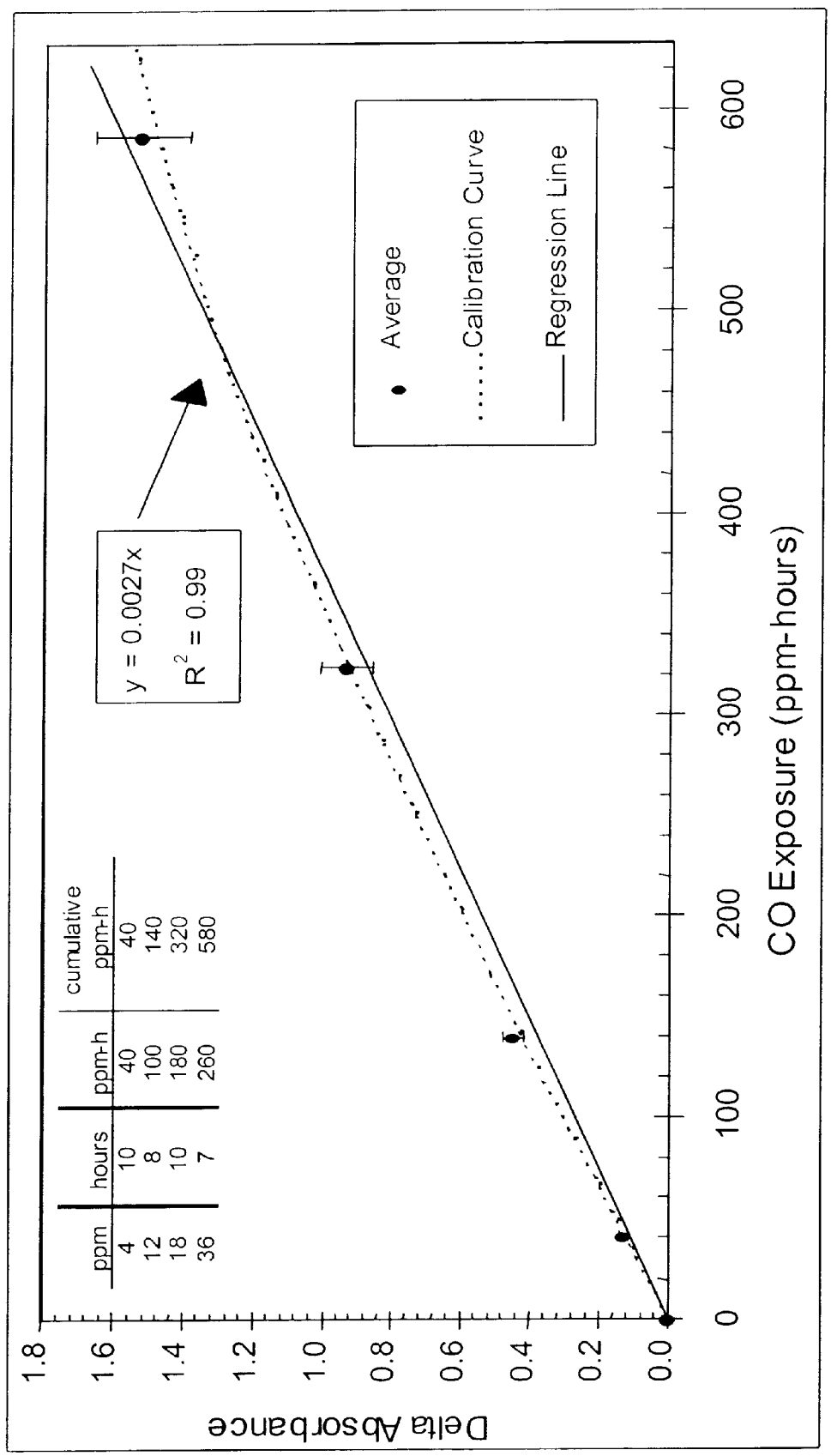
FIG. 13. Laboratory test results for the occupational dosimeter configuration of PS3/D1 passive samplers. Five samplers were exposed to CO from 40 to 600 ppm-hours in dry conditions. The dashed line (1320) indicates the sensor calibration curve derived from direct method tests. The solid line (1330) is a least-square regression fit to the average sampler response. The CO exposure data are presented in order in the superimposed table (1310). Note that exposure concentrations ranged from 4 to 36 ppm.

FIG. 13 presents the results from exposing five D1 samplers. The dosimeters' exposures ranged from 40 to almost 600 ppm-h. (To place this in perspective, NIOSH recommends that a suitable measurement range for sampling should be 0.1 to 2 times the regulatory standard, i.e., a range of 40–800 ppm-h based on the OSHA PEL, or 25–500 ppm-h based on the ACGIH TLV (Kennedy, 1995)). The actual concentrations and duration of the test exposures are tabulated (1310) in FIG. 13. The concentrations ranged from 4 to 36 ppm. The highest exposure led to a delta absorbance average of more than 1.5 A, which was out of the linear region of the sensor response curve. The dashed curve (1320) superimposed on FIG. 13 is the scaled direct method response curve. Although the data clearly fit the calibration curve very well the non-linearity at the high-end of the response curve was evident. A least-square fit through all the data (1330) still indicates a reasonable (correlation coefficient, $R^2$=0.98) fit to a linear model but the use of the polynomial fit to the calibration curve provides more precision. The RSDs for the lowest and highest exposure levels were 9.9% and 8.9%, respectively. The average RSD across the exposure levels was 8.4%. The average value for the diffusion scaling factor, R, was 2.6 (RSD=7.4%), consistent with the much higher diffusion rate for the occupational dosimeter design. The slope, p, of the regression line was 0.0027 A-ppm$^{-1}$hr$^{-1}$ (95% interval (CI) of p:0.0026 to 0.0028). The low RSD for the diffusion ratio indicated that the behavior of the sampler was very consistent over the wide exposure range. As with the PS2, the data indicate that the dosimeter response to CO exposure was independent of CO concentration.

D. D2 Test Results

A series of three tests were conducted on D2 design. Sets of three dosimeters were uncapped and exposed using the diffusion sampler test method in the 3-liter reaction vessel. Three capped dosimeters were also placed in the vessel during the exposure experiments as controls. Table 4 presents the exposure conditions and average dosimeter response at 700 nm. Sets of three uncapped dosimeters and three controls were exposed in approximately 4-hour increments to 40 ppm CO (159 to 207 ppm-hours) and nominal relative humidities (RH) of 20%, 30%, 50%, or 90%. In Tests 1 and 3 the dosimeters were first exposed to low RH for 8-hours, and then high RH for 8-hours. This pattern was reversed in Test 2 where the dosimeters were first exposed to high RH and then low RH.

Figure 14:
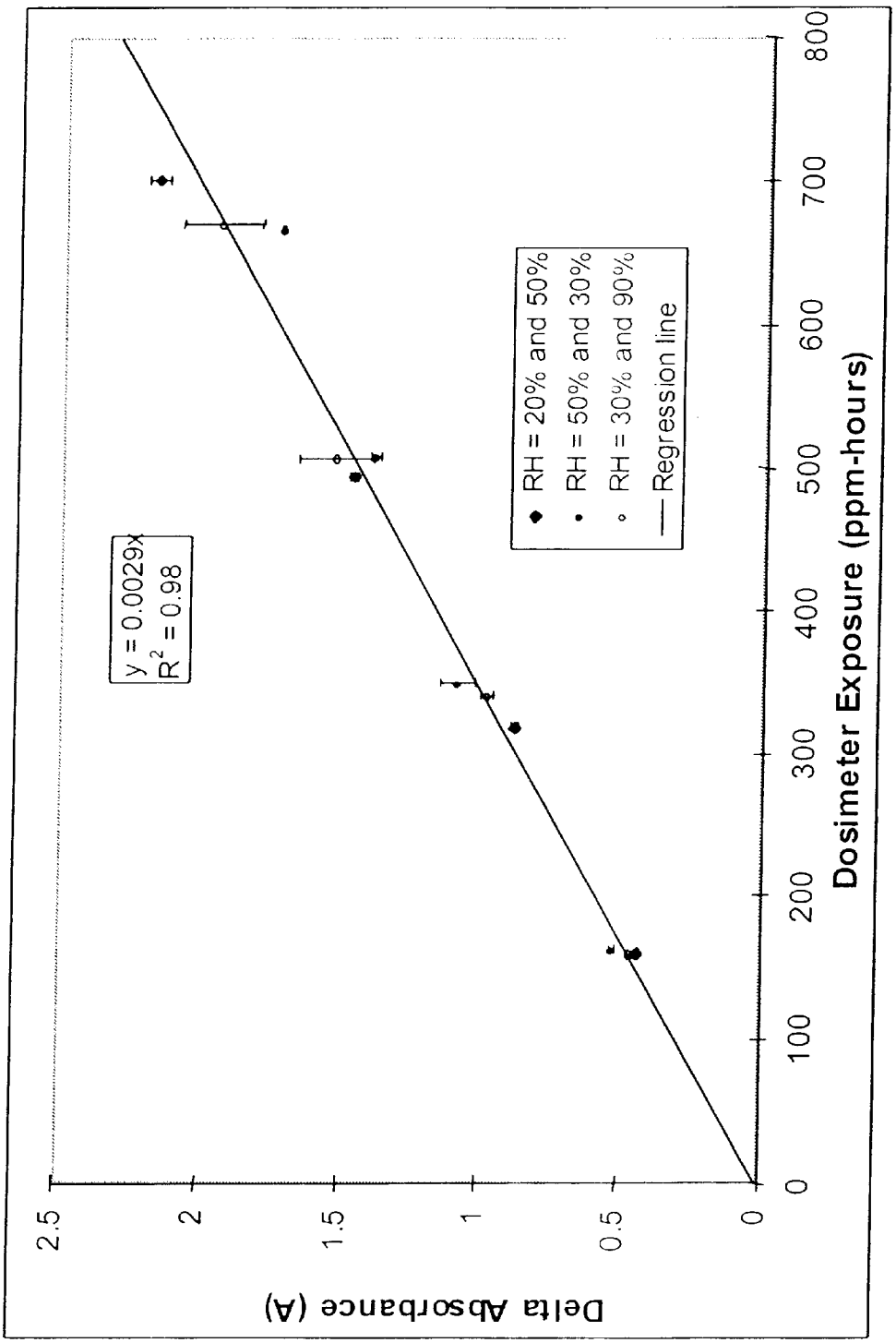
FIG. 14. Humidity test results from LBNL/QGI CO Occupational Dosimeter D2. Sets of three dosimeters were incrementally exposed to 40 ppm CO and 20%, 30%, 50%, or 90% relative humidity for two 4-hour periods. The variability in dosimeter response does not appear to be related to humidity.

FIG. 14 presents the average of three dosimeters from all three tests. Error bars represent ±1 standard deviation of the incremental (4-hr) change in absorbance of the dosimeters. The humidity exposure of each run is identifiable in the FIG. 14. A bivariate least-squares linear regression of the dosimeter response against CO exposure, with the intercept constrained to zero, indicates that the slope, p, of the average dosimeter response was 0.0029 A-ppm$^{-1}$hr$^{-1}$ ($R^2$=0.97, 95% CI of p: 0.0028 to 0.0030 A-ppm$^{-1}$hr$^{-1}$).

A multivariate regression analysis of dosimeter response against CO exposure and relative humidity is presented here. This analysis, was conducted by breaking the three tests into their incremental, nominal 4-hour, exposure increases in order to look at the unbiased relationship between CO exposure, RH, and dosimeter response. The analysis uses the 36 individual dosimeter absorbance measurements and their associated exposures and RH levels. The results yielded a CO exposure coefficient of 0.0029 A-ppm$^{-1}$hr$^{-1}$ (p<0.0001, $R^2$=0.94, 95% CI of p: 0.0027 to 0.0031 A-ppm$^{-1}$hr$^{-1}$) and an RH coefficient of 0.0006 (95% CI: 2.0×10$^{-5}$ to 0.001). The relationship between CO exposure and dosimeter response was statistically highly significant, and the effect of RH was weak but significant at the 95% confidence level. The RH coefficient suggests a change in absorbance effect of 0.06 A at 100%RH (equivalent to 20 ppm-hours). The dosimeter response coefficient, ρ, of 0.0029 A-ppm$^{-1}$hr$^{-1}$ seen in these data were very close to the slope of 0.0027 A-ppm$^{-1}$hr$^{-1}$ measured for the response of the D1 dosimeter prototype.

Although the RH effect was statistically significant in this analysis, its import is small (20 ppm-h compared with an 8-hr TLV of 200 ppm-h and PEL of 400 ppm-h, i.e., <10% of TLV and 5% of PEL). More importantly, these tests showed that the improvements in the sensor holder design had the intended effect on water vapor transfer rate. The D2 prototype was capable of operating at very high humidity without compromise to sensor performance.

Precision, bias, and accuracy calculated for the D2 prototype exposure data are also shown in Table 4. The samplers were exposed to four different humidity levels as discussed above. The precision of the samplers in these exposure experiments was very low (1%–5%) with the exception of the two discussed above that were exposed to 90%RH. The bias observed for all experiments was also low with an absolute value ranging from 0 to 10%. The accuracy calculated using the NIOSH nomogram (Kennedy, 1995) ranged from 5% to 16% except for the variable high-RH samplers which had accuracies of 20% and 27%. Interestingly, high-RH exposures did not bias the dosimeters (bias was 0 and 4% for these two exposures).

E. D3 Test Results

A series of test were conducted to investigate the effect of temperature on the LOCD response. Sets of 10 dosimeters were exposed to 25 ppm CO at temperatures of 10° C., 20° C., or 30° C., for 8-hours. The slope of the dosimeter response under these conditions is presented in Table 5. A discussion of an important observation regarding low temperature (10° C.) effects on sensor chemistry will follow below. An analysis of variance between temperature treatment groups indicates that intra-temperature variance was not statistically significant at the 95% confidence level. In contrast, the variance between temperature treatment groups was statistically significant (p=0.007). Pair-wise t-tests were conducted assuming that the variance in dosimeter response in each temperature treatment group was equal. A test of the hypothesis that the mean dosimeter response for the 10° C. group was no different from the 20° C. group was rejected (p<0.001). The 10° C. group was also statistically different from the 30° C. group (p=0.027). The hypothesis that the mean response of the 20° C. group was not different from the 30° C. group was accepted (p=0.14). An interesting finding was that the slope of 0.0034 for the 10° C. group was about 26% higher than the 20° C. group. This finding indicates that a temperature correction was necessary for dosimeters exposed in colder environments.

Table 4. LBNL/QGI occupational dosimeter (D2) humidity effects tests. These exposure tests were conducted in a 3-liter reaction vessel at 40 ppm CO and 20° C. Three series of four 4-hour exposure runs were conducted. Each test was conducted at a low and a high relative humidity (RH) level. The sequence of low and high RH exposures were alternated. Three dosimeters were concurrently exposed in each test. Average dosimeter response (±standard deviation), less average of 3 unexposed controls, at 700 nm are presented. Incremental response is between successive runs in each test. Precision, bias, and accuracy using the NIOSH definition (Kennedy, 1995) for each of the elapsed CO exposures are also included.

| Test # | Run # | Average Relative Humidity (%) | Incremental CO exposure (ppm-hours) | Average Dosimeter Response[a] (A) | Elapsed CO exposure (ppm-hours) | Average Dosimeter Response (A) | Precision | Bias | Accuracy (%) |
|---|---|---|---|---|---|---|---|---|---|
| 1 | 1 | 20 | 160 | 0.43 (±0.00) | 160 | 0.43 (±0.00) | 0.01 | −0.06 | 7 |
|   | 2 | 20 | 160 | 0.45 (±0.02) | 320 | 0.88 (±0.02) | 0.02 | −0.05 | 8 |
|   | 3 | 50 | 180 | 0.59 (±0.01) | 490 | 1.47 (±0.03) | 0.02 | 0.03 | 6 |
|   | 4 | 50 | 210 | 0.70 (±0.04) | 700 | 2.17 (±0.03) | 0.01 | 0.07 | 9 |
| 2 | 1 | 50 | 160 | 0.52 (±0.01) | 160 | 0.52 (±0.01) | 0.02 | 0.10 | 14 |
|   | 2 | 50 | 190 | 0.56 (±0.06) | 350 | 1.09 (±0.06) | 0.05 | 0.07 | 16 |
|   | 3 | 20 | 160 | 0.31 (±0.02) | 510 | 1.39 (±0.08) | 0.05 | −0.05 | 13 |
|   | 4 | 30 | 160 | 0.34 (±0.00) | 670 | 1.73 (±0.07) | 0.04 | −0.10 | 16 |
| 3 | 1 | 30 | 160 | 0.46 (±0.01) | 160 | 0.46 (±0.01) | 0.02 | −0.01 | 5 |
|   | 2 | 30 | 180 | 0.52 (±0.03) | 340 | 0.98 (±0.03) | 0.03 | −0.01 | 8 |
|   | 3 | 90 | 170 | 0.55 (±0.13) | 510 | 1.53 (±0.14) | 0.09 | 0.04 | 20 |
|   | 4 | 90 | 160 | 0.42 (±0.14) | 670 | 1.94 (±0.27) | 0.13 | 0.00 | 27 |

[a]Response to individual consecutive incremental (4-hour) exposures during exposure tests.

TABLE 5

Effect of temperature during 25 ppm CO exposure on sensor response of LBNL/QGI Occupational Dosimeters.

| Exposure Temperature | Average Slope (A/ppm-h) | Relative Standard Deviation |
|---|---|---|
| 10° C. | 0.0023[a] | 10% |
| 10° C. | 0.0034[b,c] | 11% |
| 20° C. | 0.0027[a] | 16% |
| 30° C. | 0.0029[a] | 20% |

Figure 15:
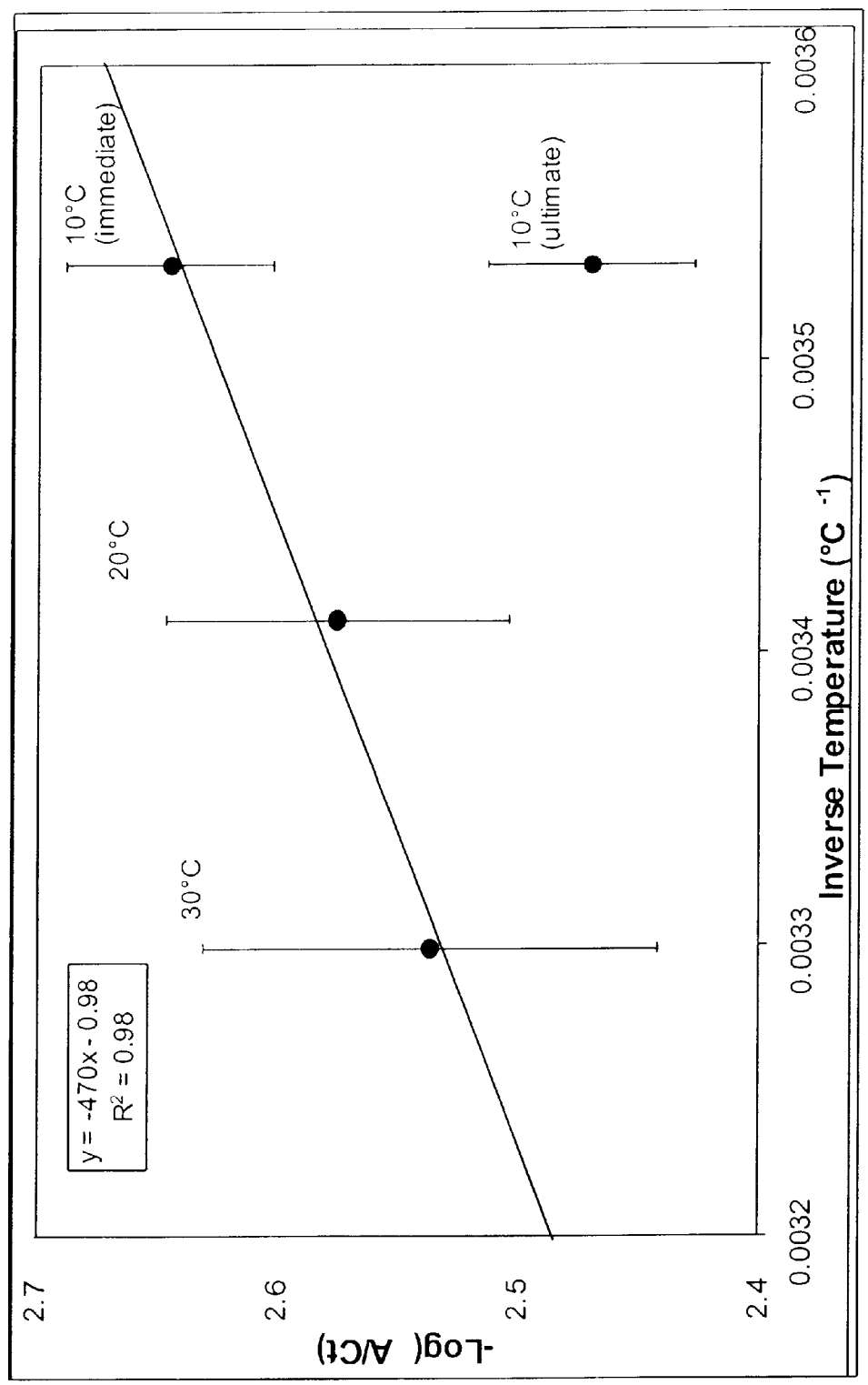
FIG. 15. Arrhenius plot of D2 CO dosimeter response as a function of temperature. A clear relationship can be seen between sensor kinetics and temperature if response (dA) is measured immediately after exposure. A latent reaction occurs in the dosimeters exposed at 10° C. once they are allowed to warm to 20° C. (see "ultimate" response at 10° C.). The (slow) Pd—Mo reaction, leading to sensor color change, is identified here as the rate-limiting step in the sensor chemistry. The CO—Pd catalytic reaction does not appear to be hampered at 10° C. A CO—Pd "complex" appears to be stored until the Pd—Mo reactions occur.

Ten dosimeters were exposed for each test.
[a]Slope calculated using sensor absorbance measured immediately after exposure test at 10° C.
[b]Slope calculated using sensor absorbance measured 12 hours after exposure test at 10° C.
[c]Statistically different from 20° C. (p < 0.001) and 30° C. (p = 0.027) slopes at the 95% confidence level When the dosimeters were exposed to CO at 10° C., their response was slow at the beginning. Absorbance measurements taken immediately after the 8-hour, 25 ppm CO exposures translated into a response slope, p, of 0.0023±0.0002 A-ppm$^{-1}$hr$^{-1}$ (see Table 5). However after 12 hours of post-exposure storage at approximately 20° C. the absorbance of the sensors increased to indicate the response slope, p=0.0034 A-ppm$^{-1}$hr$^{-1}$. This indicates that the sensors continued to interact normally with CO throughout the 10° C. exposure because the initial PdCl$_3$ oxidation of CO was not be affected by the lower temperature. The CO oxidation is thought to be a fast reaction, so it is likely that the change in reaction rate caused by the 10 degree temperature drop did not significantly affect the sensor performance. However, the sensor condition at the initial post-exposure measurements indicates that the final concentration of the blue, mixed oxidation state Mo, had not yet been reached. This verifies that the rate-limiting step in the sensor kinetics was the Pd—Mo forward reaction, and that the rate at which the Mo(VI) was reduced to the Mo blue species was significantly affected by temperature. FIG. 15 presents an Arrhenius plot, i.e., log sensor response plotted against inverse temperature, (Johnston, 1966), of the immediate-post exposure data, showing that the rate-limiting sensor kinetic was affected by temperature as would be expected. Note that the ultimate sensor response, reflecting the dA value once the dosimeters were moved to 20° C. and the Pd—Mo reactions had completed, is also plotted on FIG. 15.

Based on these results any samplers that have been exposed in environments colder than 20° C should be allowed to react to completion at room temperature prior to making a final absorbance measurement. If necessary, a series of post exposure measurements should be conducted until the sensor response stabilizes.

VI. Comparison Between Sensor Direct Test Method and Diffusive Sampler Test Method A. Forward Response Comparisons between the direct test forward response data and the response from the diffusion samplers shed light on the deviation from linear response seen in sensors exposed via the direct method. FIG. 11 and FIG. 13 show that that the responses (1120 and 1320) of the passive sampler and occupational dosimeter are both quite linear despite the non-linearity of the direct test response of sensors from the same batch. This observation bolsters the theory that the non-linearity of the direct test data is probably an artifact caused by saturation of the most available reaction sites on the sensor surface.

B. Backward Response

The rate of reversibility (regeneration) of the MD15 sensor was about one percent of their response per-day. Although acceptable for short term measurements, this reversibility was responsible for some bias due to loss of sample both during exposure, and after the samplers were capped. However, due to the empirical sampler calibration method, the sampler response slope, $\rho$, does include an average reverse reaction component. This is because the reverse reaction occurs during the test exposure period so long as comparable times are used. Thus, on average, calculated exposures of the samplers, $e_{calc}$, was not likely to have been biased by reversibility. However, due to a small degree of variability of the reverse reaction among sensors from the same batch, individual calculations of $e_{calc}$ could be biased to some extent. For the 8-hour dosimeters, the error introduced by variability in reversibility should be negligible since the average daily regeneration is only about 1 percent. For the one-week passive samplers (PSx), slightly more error could be introduced due to variability due to the longer exposure period. Clearly, due to the post-exposure reversibility, the samplers should be measured as soon as possible after exposure. If they were to be measured within one day the losses would be insignificant, but could be of concern over longer periods.

VII. Interference Test

A. Potential Interferents

A series of tests were conducted to assess the performance of the dosimeter in the presence of potential interferents. These tests were conducted using relatively high concentrations of the potential interferents. Fifteen different molecular species tested represent a fairly large range of the types of gas-phase pollutants commonly found in occupational and residential environments were selected for these tests. Table 6 presents the experimental conditions of the interference testing. These tests did not include three potential interferents: environmental tobacco smoke (ETS), aldehydes, and nitrogen dioxide ($NO_2$). The potentially interfering inorganic gases that were tested included carbon dioxide, and nitrogenous gases (nitrous oxide, nitric oxide, and ammonia). Organic compounds that were tested include alcohols (ethanol and isopropanol), aromatic hydrocarbons (toluene), alkanes (butane, methane, heptane), alkenes (ethylene), halogenated alkanes (trichloroethane), ketones (acetone), and esters (ethyl acetate). In addition, a commercial acrylic cement containing a mixture of organic solvents (including methylene chloride and methyl ethyl ketone) was tested.

B. Comparative Test Results

Paired t-tests were used to compare the mean electrochemical CO detector response (assuming an accuracy of ±5%) to the mean dosimeter response ($H_0$: $\mu_1=\mu_2$). Table 6 indicates that with two exceptions there was no strong interfering effect from the compounds tested. The two exceptions were NO and ethylene. A concentration of 50 ppm of NO, without CO, over the 2 hour exposure period caused an average decrease in absorbance of 0.24±0.03 A, corresponding to an apparent "negative" CO concentration (−80±10 ppm-h). Interestingly there was no statistically significant negative bias to the dosimeter response when CO and NO were both present in the test atmosphere (p=0.22). In the case of ethylene, the response to a two hour, 200 ppm exposure in the absence of CO produced an apparent dosimeter response of 200±90 ppm-h. When exposed to the combination of 200 ppm ethylene and 100 ppm CO the resulting apparent dosimeter response was 370±40 ppm-h. Ethylene appears to be a strong positive interferents for the dosimeter. No other interferents+CO combinations yielded statistically significant differences between actual CO concentrations and the apparent dosimeter measurements.

A number of the interferents appear to have caused small effects on the dosimeter in the absence of CO. Methane, heptane, and isopropanol appear to have caused a statistically significant (p<0.05), slightly negative dosimeter response. $CO_2$, $N_2O$, and ethyl acetate had slightly positive, statistically significant (p<0.05) dosimeter response. Possibly, the effects seen here were an artifact of the small sample size (3 dosimeters) used in these tests. Certainly, the practical significance of these small effects is likely to be negligible. Recall that the concentrations of these potential interferents were quite high relative to those found in typical occupational and residential settings.

TABLE 6

Prototype D3 LBNL/QGI Occupational Carbon Monoxide Dosimeter (LOCD) response in the presence of potentially interfering gases.

| Interferent or interferent + CO | Interferent Concentration (ppm) | Actual CO Exposure (ppm-hours) | Apparent CO Exposure, LOCD (ppm-hours) | Average Relative Humidity (% RH) | Average Temperature (° C.) |
|---|---|---|---|---|---|
| CO alone | 0 | 110 | 83 ± 30 | 30 | 25 |
| CO alone | 0 | 280 | 280 ± 60 | 10 | 26 |
| carbon dioxide[†] | 1100 | 0 | 10 ± 0 | 30 | 27 |
| carbon dioxide + CO | 1000 | 200 | 200 ± 20 | 30 | 26 |
| nitrous oxide[†] | 230 | 0 | 10 ± 0 | 20 | 27 |
| nitrous oxide + CO | 200 | 220 | 260 ± 30 | 20 | 26 |
| nitric oxide[††] | 50 | 0 | −80 ± 10 | 20 | 26 |
| nitric oxide + CO | 50 | 220 | 200 ± 20 | 20 | 25 |
| Ammonia | 80 | 0 | 0 ± 10 | 30 | 26 |
| Ammonia + CO | 100 | 220 | 220 ± 20 | 20 | 26 |
| Ethanol | 150 | 0 | 10 ± 0 | 10 | 26 |
| ethanol + CO | 150 | 250 | 190 ± 70 | 10 | 25 |
| Isopropanol[†] | 160 | 0 | −10 ± 0 | 20 | 27 |
| Isopropanol + CO | 160 | 220 | 260 ± 110 | 20 | 26 |
| Ethylene[††] | 200 | 0 | 200 ± 90 | NA | NA |
| Ethylene + CO[††] | 200 | 210 | 370 ± 40 | 30 | 26 |
| Toluene | 170 | 0 | 10 ± 10 | 20 | 26 |
| toluene + CO | 170 | 190 | 200 ± 20 | 20 | 26 |
| Butane | 270 | 0 | 10 ± 0 | 30 | 25 |
| butane + CO | 300 | 200 | 200 ± 10 | 20 | 27 |
| Methane[†] | 480 | 0 | −10 ± 10 | 30 | 26 |
| Methane + CO | 530 | 220 | 230 ± 40 | 30 | 27 |
| Heptane[†] | 470 | 0 | −10 ± 0 | 30 | 25 |
| Heptane + CO | 470 | 210 | 230 ± 30 | 30 | 27 |
| Trichloroethane | 270 | 0 | 0 ± 0 | 30 | 28 |
| Trichloroethane + CO | 280 | 230 | 230 ± 60 | 20 | 26 |
| Acetone | 200 | 0 | 0 ± 0 | 30 | 26 |
| Acetone + CO | 180 | 210 | 220 ± 40 | 20 | 26 |
| ethyl acetate[†] | 190 | 0 | 10 ± 0 | 30 | 26 |
| ethyl acetate + CO | 190 | 210 | 220 ± 10 | 20 | 26 |
| acrylic cement[a] | [b] | 0 | 10 ± 0 | 30 | 24 |
| acrylic cement + CO | [b] | 220 | 230 ± 10 | 30 | 25 |

Exposures were conducted in a 500 liter stainless steel and glass glove box.
[a]Commercial product containing a mixture of organic solvents including methylene chloride and methyl ethyl ketone.
[b]Estimate: 2300 ppm DCM and 2000 ppm MEK generated by spreading 20 grams of acrylic cement on a metal foil surface in exposure chamber.
[†]$p < 0.05$, results of paired t-tests with $H_0: \mu1 = \mu2$.
[††]$p < 0.005$ results of paired t-tests with $H_0: \mu1 = \mu2$.

VII. Sampling Rate Validation

The empirical methods for calculating the passive sampler response characteristics were all that was needed to calibrate the device. However, that technique provides no information on the mass of CO that was involved in the reactions at the sensor surface. Actual sampling rates could not be calculated unless these molecular quantities were known. A controlled mass balance experiment was devised to measure the relationship between mass of CO molecules reacted in the forward reaction, to the observed change of sensor absorbance. Theoretically, this relationship should be constant for a batch of sensors:

$$\beta = \frac{dA}{M} \quad (12)$$

where, $\beta$ = change in sensor absorbance per microgram of CO ($A \cdot \mu g^{-1}$), dA = change in absorbance of QGI sensor at 760 nm (A), and, M = mass of CO reacted at the sensor surface ($\mu g$).

The slope, $\rho$, of the actual passive sampler response to CO exposure is an important parameter. Symbolically it is expressed as the ratio presented in Equation 10:

$$\rho = \frac{dA}{e}.$$

In the case of multiple CO exposures of one or more samplers, p ($A \cdot ppm^{-1} hr^{-1}$) is the slope of a regression line fitted to the relationship between dA and exposure (ppm-h).

An empirical mass conversion rate can be calculated for the diffusion samplers once a value for b is determined:

$$q_{emp} = \frac{\rho}{\beta} = \frac{dA/e}{dA/M} = \frac{M}{e} \quad (13)$$

where, $q_{emp}$ = the empirical, dosimeter mass conversion rate ($\mu g \cdot ppm^{-1} hr^{-1}$).

When the units of exposure are expressed in terms of mass, a volumetric sampling rate can be calculated:

$$q_{empv} = \frac{M}{e} = \frac{\mu g}{(\mu g \cdot m^{-3})hr} = \frac{10^6 \cdot cm^3}{hr} \qquad (14)$$

where the units of $q_{empv}$ are $cm^3\ hr^{-1}$.

Note that volumetric concentrations in ppm can be converted to mass concentrations by applying the Ideal Gas Law. Given the molecular weight of CO is 28 g-mole$^{-1}$, and assuming a temperature of 20° C. and 1 atmosphere, 1 ppm of CO=1162 $\mu$g-m$^{-3}$.

Dosimeters constructed using the final mass-producible configuration (LOCD) were exposed to a measured volume of CO using the following protocol. A rubber GC septum was fitted to a port on a 1-liter glass desiccator vessel with ground glass sealing flanges. The initial absorbance of ten dosimeters was measured. They were then placed in the vessel. A precision gastight syringe was filled with 10.00 ml of 5000±50 ppm (5.8 $\mu$g) CO (Matheson Primary Standard grade gas mixture). This gas was injected into the vessel. Preliminary experiments using a similar method, which allowed for direct measurement of the dosimeter without interruption of the exposure, showed that one dosimeter fully reacts 2.00 ml of 5000 ppm CO within 4 days. Thus, once the CO was injected into the vessel, the dosimeters were exposed, uninterrupted, for 4 days. At the end of the fourth day the dosimeters were removed and their final absorbance at 700 nm was measured. The average mass of CO consumed by each dosimeter was calculated using the Ideal Gas Law (1 m CO (pure)=1162 $\mu$g at 20° C. and 1 atmosphere). The ratio, B, was calculated for each dosimeter.

In a subsequent event, set of 10 LOCD were exposed in the desiccator. On average, each sensor reacted with 1000 ml of the gas mixture, equivalent to 5.81 $\mu$g of CO. The sensor absorbance at 700 nm changed by an average of 0.35±0.07 A. Thus, the empirical mass conversion rate, B, was 0.060±0.011 (A-$\mu$g$^{-1}$) and the empirical mass conversion rate, $q_{emp.}$, from Equation 13 was 4.5×10$^{-2}$±0.9×10$^{-2}$ $\mu$g-hr$^{-1}$ppm$^{-1}$. Using Equation 14 this translates into a volumetric sample rate of 39.0 cm$^3$-hr$^{-1}$.

The theoretical mass conversion rate q, for a diffusion sampler configured (L=4.065 cm and $A_x$=0.18 cm$^2$) as a D3 dosimeter, calculated using Equation 7, is 4.6×10$^{-2}$ $\mu$g-ppm$^{-1}$hr$^{-1}$ (39.6 cm$^3$-hr$^{-1}$). Clearly, $q_{emp.}$ and q were very close: the measured CO sampling rate was within 2% of the theoretical rate indicating that the overall efficiency of the dosimeters was about 98% in laboratory testing.

EXAMPLE 1

Field Testing of PS1 and PS2

To test the overall performance of the prototype CO passive samplers, field tests were conducted over one-day to one-week periods using the following protocol: Two to five passive samplers or occupational dosimeters and one or more field and laboratory controls were used at each site. An air sampling bag reflecting the integrated time-weighted-averaged concentration sampled at a constant rate of 0.5 cc-min$^{-1}$, so in the course of a week about 5 liters of air were collected.

The air samples in the bags were analyzed directly using the Thermo Environmental Model 48 Gas Filter Correlation CO Analyzer. This analyzer operates at a flow rate of 1.0 l-min$^{-1}$ and provides updated concentration readings every 10 seconds. When sampling from the air sample bags, the measurement reaches steady-state within two minutes. The one-week integrated air sample concentration was determined from the average of twelve 10-second-average analyzer readings over the third-through fourth minutes of measurement.

The absorbance of passive sampler sensors exposed in the field were measured using the spectrophotometer before and after deployment. The change in absorbance of the sensors was used to determine the exposure.

Figure 16:
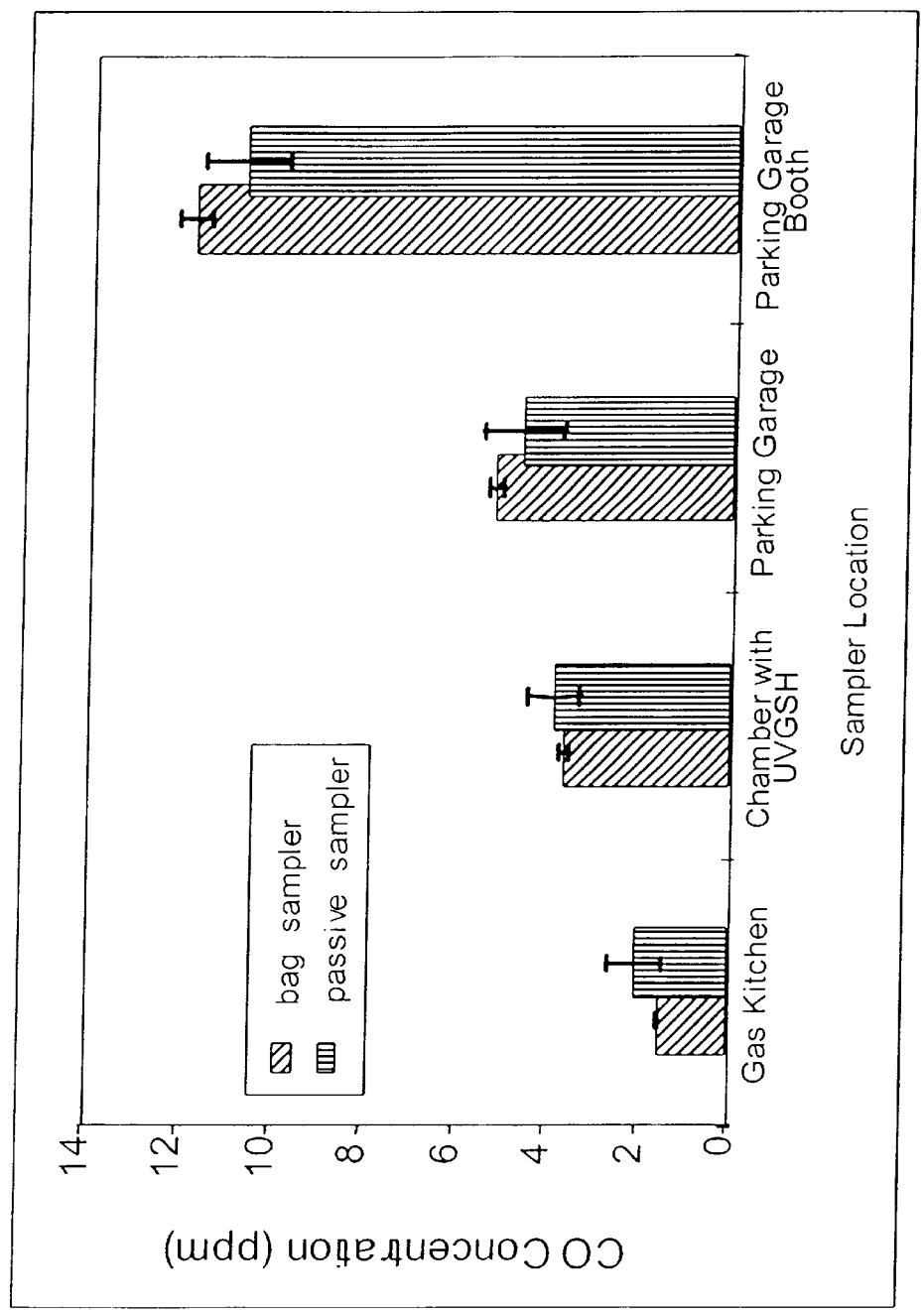
FIG. 16. Combined preliminary field test results from PS1 and PS2 LBNL/QGI CO passive samplers in four indoor environments. These results are compared to average CO concentrations collected using bag sampler and analyzed using a gas-filter-correlation CO analyzer.

FIG. 16 summarizes the field performance data using both PS1 and PS2. One field site was tested using two PS2 samplers and one P2 control. The results of this test, in a day-use parking garage were excellent and consistent with the measurement conducted using the PS1. The one-week average CO concentration in the garage was 5.2±0.2 ppm as measured in bag samples. The average concentration measured by the passive samplers was 4.6±0.9 ppm. The RSD of the two sampler measurements, after adjusting for the control was 19.8%. The mean concentration as measured by the samplers was about 0.6 ppm lower than the bag sampler. It should be noted that the RH in the samplers was about 50% indicating that humidity does not seem to have interfered with the sensor. Also, it is likely that a wide mix of organic compounds and combustion products were present in the garage since a large number of automobiles were parked in or drove through the space. These compounds do not appear to have interfered with the performance of the sampler.

EXAMPLE 2

Field Testing of D3

Three field tests were conducted using the D3 occupational dosimeter in residential environments prior to conducting tests in true occupational environments. The dosimeters were operated as area samplers for periods of two to three days during these tests. At each site three dosimeters were exposed and one bag sample was collected. Once deployed, the dosimeters were mounted on the bag sampler case next to its inlet port. Three additional dosimeters, used as controls, were placed next to the bag sampler but were not exposed.

Figure 17:
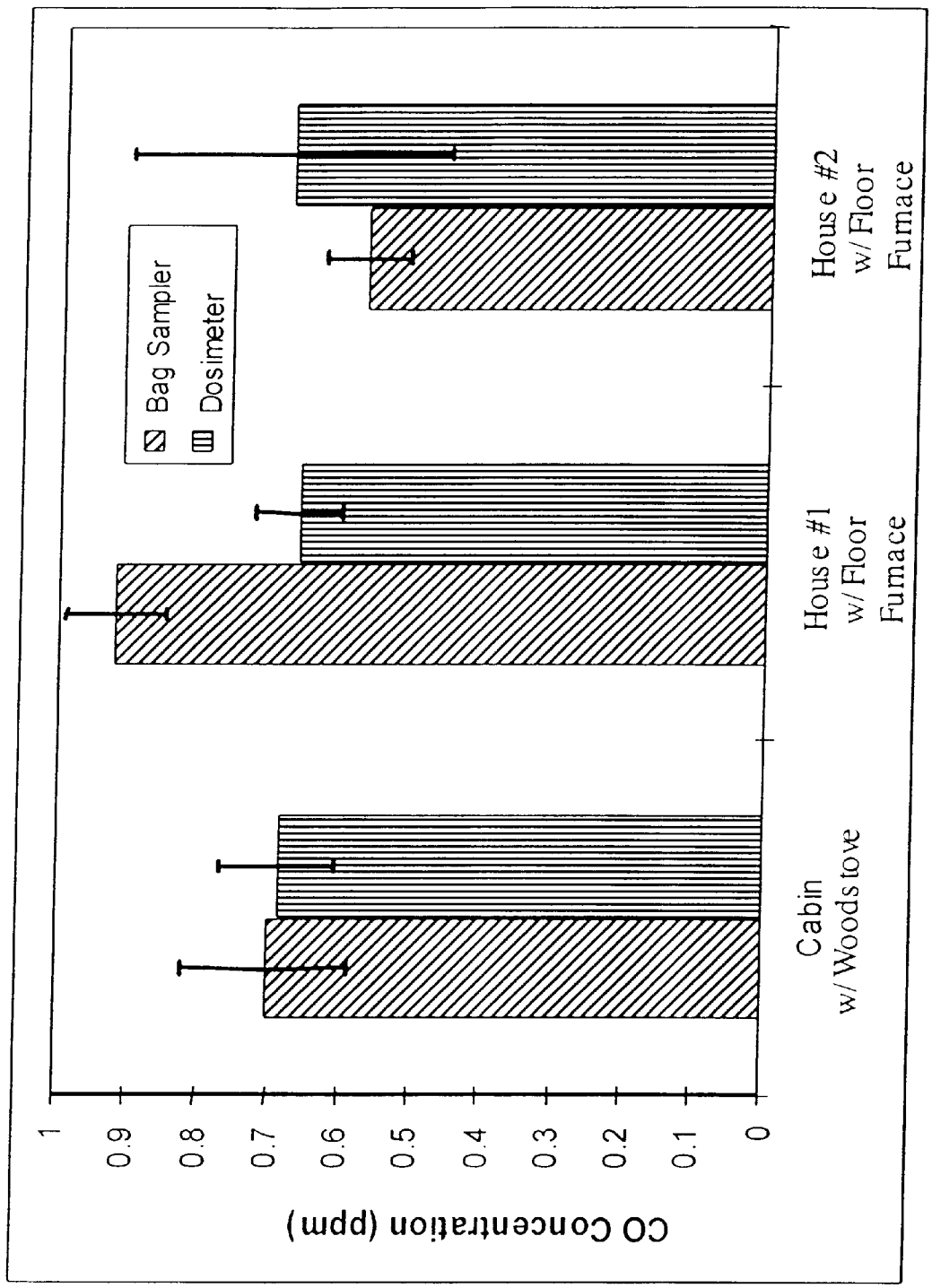
FIG. 17. Comparison of LBNL/QGI Occupational Dosimeter measurements and bag sampler measurements made in three residences. The dosimeter results are the average of three dosimeters in each case. The error bars indicate plus and minus 1 standard deviation. The bag and dosimeter samples were collected concurrently at the same location for a period of approximately three days at each site FIG. 18. LBNL/QGI CO Occupational Dosimeter (LOCD) vs. Bag Sampler Data collected at fixed-sites throughout the Moscone convention Center during the CO exposure study. Air samples were collected in Tedlar Bags over an 8-hr period, and analyzed using a Gas Filter Correlation CO analyzer. Three LOCD were deployed at the site of each bag sampler. The error bars represent ±one standard deviation about the mean LOCD value.

FIG. 17 presents the results of the bag sampler measurements compared to those from the dosimeter. All three residences; one cabin in a rural setting, and two urban houses, had potential CO sources, however the average CO concentration at all three sites were quite low during the measurement periods. The cabin was heated with a non-airtight wood stove while the two houses used floor furnaces. The exposure, $e_{calc}$, was calculated by applying equation 10, and using the empirically derived value of p=0.0027 A-ppm$^{-1}$hr$^{-1}$. The time-weighted average CO concentrations were 0.69±0.08 (RSD=12%); 0.66±0.06 (RSD=9%), and 0.68±0.22 (RSD=33%) for the cabin, House #1, and House #2, respectively. Although humidity levels were not monitored during any of these tests they were probably quite high because they were conducted during rainy weather in the 1996–97 winter season.

These results indicated that the dosimeters are accurate at very low CO exposures and can operate over longer periods of time than the 8-hour period that they were designed for. No noticeable change was evident in the color of the dosimeters' blue indicator desiccant after these protracted exposures, indicating that the drying capacity of the gel had not diminished.

EXAMPLE 3

Field Validation

In order to assess the performance of present invention, a field validation study through actual industrial hygiene measurements and comparison against a standard CO measurement method was conducted. The details of this study are reported elsewhere (Apte, 1999) but information relevant to this invention is presented below.

A. Relevant Occupational Health Standards

Federal OSHA Permissible Exposure Limit (PEL) for CO is set as a time-weighted-average (TWA) of 50 ppm for an 8-hour shift (OSHA, 1993). The Cal/OSHA PEL for CO is 25 ppm TWA over an 8-hour workshift (Cal/OSHA, 1997). The Biological Exposure Index (BEI) recommended by the American Congress of Governmental Industrial Hygienists, is designed to ensure that blood carboxyhemoglobin (COHb) levels remain below 3.5% (ACCGIH, 1991). The TLV of 25 ppm is set so that an 8-hour CO exposure will not allow the BEI of 3.5% COHb to be exceeded.

B. Physical Characteristics of Field Test Site

The study was conducted during a tradeshow setup at the Moscone Convention Center (MCC) located in downtown San Francisco, Calif. The MCC occupies the space of two city blocks, with halls to the North and South of Howard Street. Overall the MCC contains over 110,000 m$^2$ (1.2 million ft$^2$) of floor area. The main underground exhibition hall space of North and South Halls have 17,000 m$^2$ (181,000 ft$^2$) and 25,000 m$^2$ (261,000 ft$^2$) of floor area. A tunnel system leads from the street level down to the subterranean hall level provides semi truck access to three loading docks with a total of 20 docking bays. The major indoor CO sources at the MCC were (1) the approximately 40 propane-powered forklifts used to move materials throughout the space, and (2) the semi trucks used to deliver and remove materials via the interior docks.

C. Participant Selection

Participants for personal sampling were selected in order that an approximately representative proportion of workers from each job category at the MCC would be monitored. Participants from each category were taken on a first-come, first-serve basis until the number for each category was reached. The participants were notified of the survey by union and management representatives and offered the opportunity to volunteer. Table 7 lists the job categories for which workers were monitor for CO during the three days of the study.

TABLE 7

Job Categories for which workers were monitored for 3 days at the Moscone Convention Center

| Job Title | Number of personal samples collected[1] |
|---|---|
| Attendant | 33 |
| Desk Worker | 4 |
| Dock Foreman | 12 |
| Dumpmeister | 2 |
| Forklift Operator | 17 |
| General Foreman | 7 |
| Handyman | 6 |
| Installer/Decorator | 49 |
| Rigger | 4 |
| Shop Steward | 3 |
| Supervisor | 11 |
| Truck Driver | 1 |
| Walker | 5 |

[1]Some participants were monitored on one, two or three days so that the actual number of participants was less than the number of workshifts monitored.

D. LBNL Measurements

1. Preparation of the Present Invention for Field Validation Study

Eighty-five LOCD (D3) were assembled with eighty-five QGI's non-regenerative CO sensor type MD-15. Wire clip holders were embedded into the dosimeter sealant during assembly to allow the device to hang from lapel clips. Each LOCD was labeled with a unique identification number. The LOCD caps were pressed firmly in place to ensure that they would not leak prior to deployment. Metal lapel clips with vinyl straps were looped through the LOCD clip holders and snapped into place so that the LOCD could be attached to the lapels of the participants.

Once manufactured, each LOCD was placed in the spectrophotometer for replicate 700 nm absorbance measurements. Prior to these measurements the spectrophotometer had been adjusted to read 0.000 A with a LOCD containing no sensor. The average of the initial absorbance measurements was about 1.5 A.

During the three days of the study, the LOCDs were reused each day. This was possible since the LOCD could be reused reliably until the capacity of the sensor was reached (an absolute absorbance of about 2.5 A–3.0 A), or the silica gel desiccant in the devices was depleted (blue indicator in gel turned clear). Five LOCD were used as controls each day. About 55 were exposed as personal monitors attached to the breathing zone of the study participants. 15 LOCD were attached, in sets of three each, to five bag samplers for fixed-site measurements within the MCC.

At the time of deployment, the LOCDs were uncapped, and the sample identification numbers and deployment times were recorded in conjunction with the anonymous participant information. At the end of the workshift sampling period the LOCDs were retrieved from the participants and capped. Sampling finish times were recorded. The LOCD identification numbers were recorded on the anonymous survey questionnaire, as described above.

2. LOCD Analysis

At the end of each day's workshift the LOCD were transported back to LBNL for analysis. The 700 nm final absorbance of all of the dosimeters were measured within 3 hours of the end of measurement. Since the devices were re-used each day, the final 700 nm absorbance measurement for the previous day was used as an initial absorbance measurement for the next set of exposures.

CO exposures were calculated by dividing the measured change in absorbance, $\partial A$ by the empirically derived response slope $\rho$. The value $\rho=0.0029$ A-ppm$^{-1}$h$^{-1}$ was derived from laboratory exposures at 20° C. of the D3 (LOCD) dosimeters using the same AW lot of sensors. This value was used to calculate CO exposures from the response of dosimeters used for personal monitoring. When the D3 dosimeters were exposed at 10° C. the effective slope of the dosimeter response was $\rho=0.0034$. This value was used to calculate the CO exposures of dosimeters which were used at fixed sites in parallel with bag samplers because the temperature inside the MCC was considerably lower than 20° C. during the sampling periods.

3. The Bag Sampler

The bag sampler is a very simple device used to collect a sample of CO laden air into an inert gas sample bag over a period of time. The sampler draws at a constant rate so that the concentration of CO in the bag at any time is the average of the sampled bulk-air concentration over that time. Since CO is a non-reactive gas, the sample is not subject to wall loss due to surface reactions. Thus, as long as the bag does not leak, bag samples of CO can be stable over a long time.

The bag samplers used in this study were designed and constructed at LBNL. They were outfitted with peristaltic pumps (Masterflex™, Cole Parmer, Niles, Ill.) with a flow rate setting of about 10 cc-min$^{-1}$. The bag samplers were built into a small plastic suitcase and were powered externally using 110V AC. The internal cavity of the suitcase was large enough to hold an inflated 10 liter air sampling bag (Air Sampling Bag, Tedlar, SKC Inc., Eighty Four, Pa.). The inlet tubing of the pump was connected via a bulkhead fitting to the side of the sampler case. The inlet fitting contained a coarse metal screen used to keep insects and large particles from entering the sampler. Tubing from the outlet of the pump was fitted with a luer compression fitting which could be directly connected to a valved fitting on the sampling bag. Tedlar air sampling bags were purged twice with dry pure air and evacuated in preparation for sampling.

During this study the bag samplers were placed at a selected fixed site within the MCC and power was provided via an extension cord. Samplers were prepared by placing a bag into the sampler case and connecting it to the outlet of the pump. Sampling commenced when the bag valve was opened allowing a constant flow of ambient air to enter the bag.

Once an air sample was collected it was analyzed using a gas-filter correlation CO analyzer which is maintained in the laboratory. This analyzer was calibrated prior to each use. The analyzer draws gas sample at a rate of about 1.0 L/m. The bags of gas samples collected at the MCC were analyzed within one day of collection. The gas-filter correlation CO analysis method is certified by the U.S. EPA for ambient air monitoring. It is documented to be accurate to ±1 percent for normal CO samples. The bag sampler and CO analyzer measurement combination was considered to be the "Gold Standard" for this. One problem with the bag samplers used in this project is that they occasionally leak or fail to fill, causing a loss of data.

4. Dräger Diffusion Tubes

The Dräger diffusion tube (Drägerwerk, Lübeck, Germany) is a standard device for measurement of workplace CO exposure. It is a sealed glass tube packed with silica gel beads impregnated with a CO sensitive color indicator. It has a graduated scale printed on it which represents CO exposure in ppm-h, with a minimum graduation of 50 ppm-h. The device is not recommended for exposures times beyond 8-hours. It is deployed by breaking the glass seal at the inlet end of the tube. The tube is typically worn by the worker throughout the work shift. Although these devices are easy to use, they have been found to have poor accuracy and statistically significant humidity effects (Hossain and Saltzman, 1989). These were placed on the lapel of each participant and a LOCD was paired to each one.

Cal/OSHA PEL is a 25 ppm TWA for an 8-hour workshift. Application of the Cal/OSHA adjustment for 12 and 16 hour workshifts would reduce the PEL to 16.7 ppm and 12.5 ppm, respectively.

E. Results

Throughout the study the level of interest and cooperation from the MCC management, the unions, and the participants was high. The workers showed considerable attention to their work environment, and concern over how it might be affecting their health. Additionally the MCC management showed interest in ensuring that the workers were protected from emissions from CO sources. All of the MCC ventilation systems were clearly operating at a high rate during our visit, based on the palpable movement of air in many parts of the building.

1. Area Measurements Using Bag Sampler and LOCD

Table 8 presents summary data from the fixed-site CO monitoring in the MCC. The measurements were time-weighted 8-hour averages taken during the work days indicated in the table. The data indicate that the level of agreement between the bag samples, analyzed using a CO analyzer, and the average of 3 LOCD was within 2 ppm and all but 1 were within 1 ppm. The highest fixed-site CO measurements were all at the docks, the highest of which were observed on the Green Dock on January 3 and 6. The bag sampler data (LOCD data) were 11 ppm (11 ppm) and 13 ppm (15 ppm) on these days, respectively. The lowest workday CO averages were observed in the North and South Halls. The set of three LOCD attached to bag sample number 5, located at the North end of South Hall, averaged 7±2 ppm (the bag sampler at this location failed).

TABLE 8

LOCD and Bag Sampler Fixed-site Monitoring Carbon Monoxide Data from the Moscone Convention Center CO Study, January, 1997.

| Bag Sample Number | LOCD Average Concentration (ppm)[a] | Bag Concentration (ppm) | Location | Date |
|---|---|---|---|---|
| 1 | 4 ± 1 | 3.5 | Red Dock | 1/3/97 |
| 2 | 11 ± 1 | 11 | Green Dock | 1/3/97 |
| 3 | 5 ± 2 | 5.4 | Red Dock at trash Compactor | 1/3/97 |
| 4 | 3 + 1 | 2.2 | North Hall (Hall E) | 1/3/97 |
| 5 | 7 ± 2 | NA | South Hall (North end) | 1/3/97 |
| 6 | 1 ± 1 | NA | North Hall | 1/5/97 |
| 7 | 3 ± 1 | 3.6 | Green Dock at desk | 1/5/97 |
| 8 | 3 ± 3 | 2.8 | Red Dock (East end) | 1/5/97 |
| 9 | 2 ± 1 | 3.0 | Breezeway between Green Dock and South Hall | 1/5/97 |
| 10 | 2 ± 2 | 2.9 | Floor 1 Lobby | 1/5/97 |
| 11 | 15 ± 3 | 13 | Green Dock at desk | 1/6/97 |
| 12 | 3 ± 1 | 4.1 | Red Dock at Supervisor Desk | 1/6/97 |
| 13 | 4 ± 1 | 3.5 | Red Dock (East end) | 1/6/97 |
| 14 | 4 ± 1 | 5.2 | Breezeway between Green Dock and South Hall | 1/6/97 |
| 15 | 3 ± 0 | 2.1 | North Hall (Northwest corner) | 1/6/97 |

[a]Average of three LBNL/QGI Occupational Carbon Monoxide Dosimeters

Figure 18:
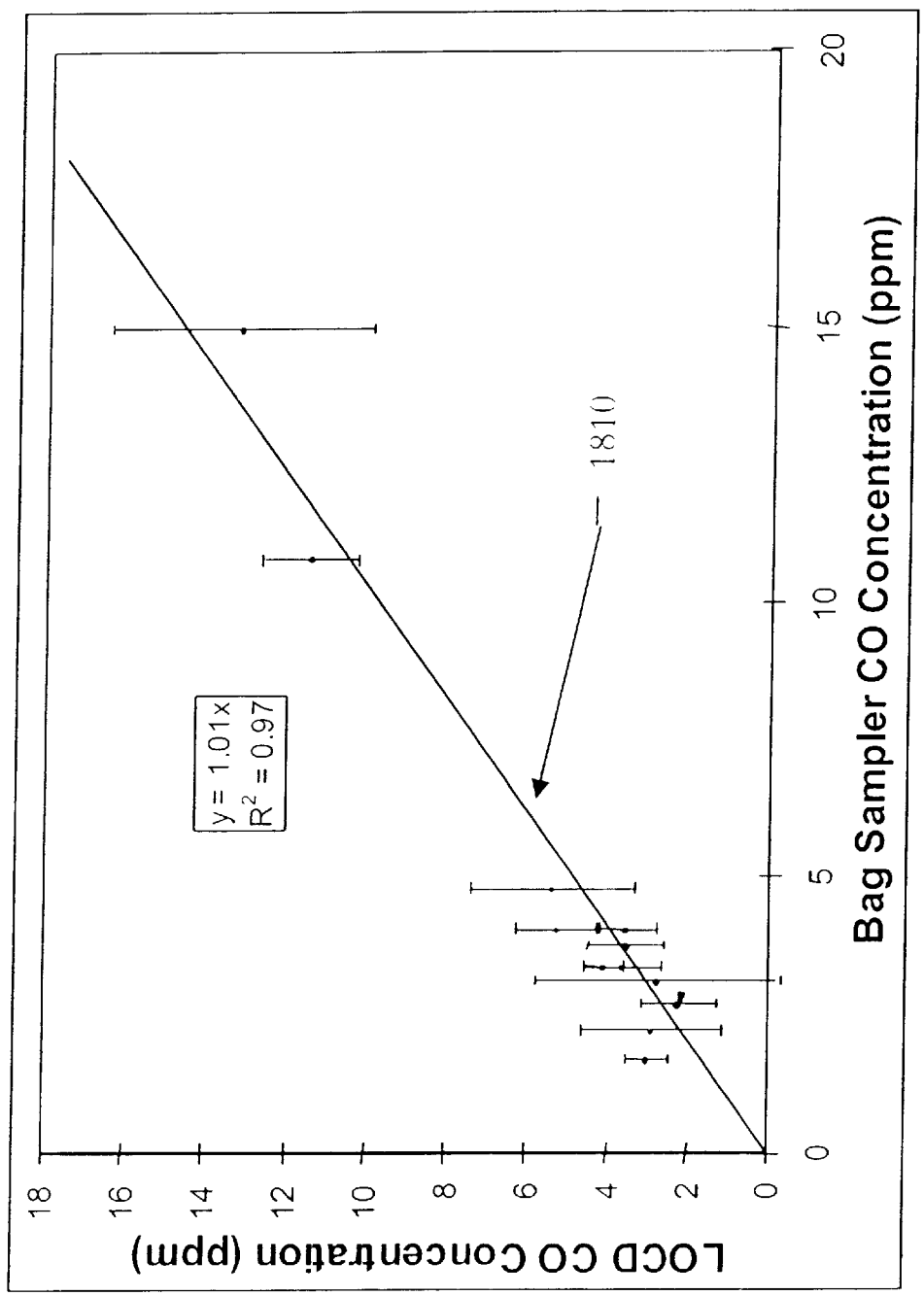

The bag sampler vs. LOCD data are plotted in FIG. 18. The error bars represent ±one standard deviation about the mean of three LOCD measurements. The average LOCD data clearly fitted the bag sample well with essentially no bias: the slope of the fitted regression line (1810) was 1.01 (95% confidence interval 0.92 to 1.1). The response was also very linear within the range of measurements ($R^2=0.97$). The average absolute difference between all individual LOCD measurements and the bag samplers was 1.2±1.0 ppm. The average absolute difference between the average of three LOCD measurements and their corresponding bag samplers was 0.7±0.4 ppm. Finally the average of all thirteen pairs of the fixed-site LOCD and bag samples were extremely similar, 4.8±3.8 ppm and 4.8±3.5 ppm, respectively.

The temperature in the MCC was colder than 20° C. during the study. Unfortunately, detailed temperature measurements were not recorded during the study. Several spot temperature measurements, taken at the Crawford and LBNL operations desk, ranged from 17.8° C. to 18.9° C. However, the operations desk was located in an enclosed internal hallway and had less ventilation air supplied, and so was observed to be considerably warmer than the loading docks and interior of the building. The average outside air temperatures for San Francisco, Calif. on January 3, 5, and 6 were 13° C., 9° C., and 11° C., respectively (NOAA, 1997). During the study, the ventilation systems were set to supply 100% outside air and were operating at a noticeably high rate, providing a continuous supply of cold air. It is estimated that the indoor temperature in the MCC was between 10° C. and 15° C. during the study. Thus, the value of $\rho=0.0034$, derived for exposures at 10° C. was used to calculate the CO exposures for the fixed-site dosimeters.

2. Personal Monitoring of Workers Using the LOCD

Occupational exposures often follow a log-normal distribution. Log-normality in the distribution of exposures to air pollutants in space and time arises from the multiplicative interaction of a series of random variables such as source, ventilation and worker mobility (Rappaport, 1991). It was expected that CO exposures measured in this study might follow a lognormal distribution. This was investigated in order to determine the appropriate statistical model with which to present the data.

Figure 19:
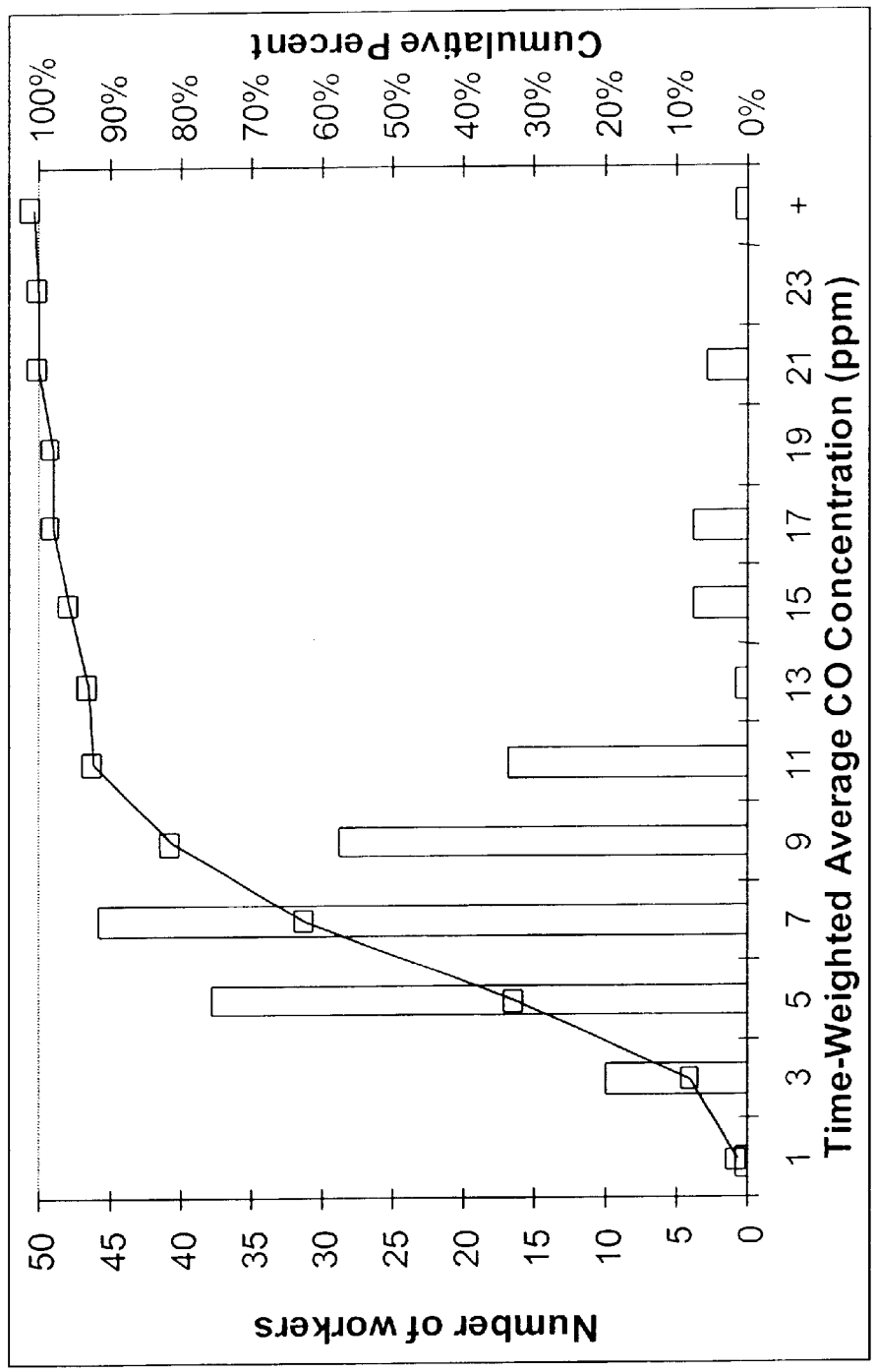
FIG. 19. Carbon Monoxide Exposure Distribution at the Moscone Convention Center during the setup of a large trade show. All Job Titles, all three days of the CO exposure study.

The distribution of all personal CO exposures measured in this study using the LOCD can be seen in FIG. 19. The long right hand "tail" of high CO concentrations seen in FIG. 19 is characteristic of a log-normal distribution (a normal distribution would appear to be more symmetrical about the mean value). These data were tested to verify whether they were better represented by a normal or log-normal model using a graphical method (Becker, Chambers and Wilkes, 1988).

Analysis of the log-transformed data shown in FIG. 19 are quite linear ($R^2=0.98$), indicating that the data are approximately log-normally distributed and that geometric statistics are probably appropriate for representing the data.

Table 9 presents the dosimetry data summarized by job category. The highest GM was observed in the group of Forklift Operators. This group of workers had a GM of average shift exposures of 9 ppm (1.6), and the maximum 8-hour exposure was 34 ppm. The $90^{th}$-percentile of Forklift Operator exposures was 17 ppm, and one of these workers (6% of Forklift Operators) had a measured 8-hour exposure in excess of the 25 ppm 8-hour PEL.

Dock Foreman and Walker and Handyman job categories had the second highest maximum observed 8-hour TWAs of 20–21 ppm ($90^{th}$-percentile was 19 ppm). From Table 9 it is evident that the Dock Foreman, Walkers, and Handyman categories [GMs of 8 (1.7) and 9 ppm (1.7), 8 ppm (1.8), respectively] had similar exposures to those of the Forklift Operators [GM=9 ppm (1.6)]. The Dumpmeister and Supervisor categories also had similar exposure means but lower variability and maximum values. The combined data for Dock Foreman and Walker and Handyman jobs were not statistically different from the Forklift Operators (Student's two-tailed t-test, p=0.89). Although only one workshift measurement was made of the exposure of a Truck Driver, the TWA exposure for this worker was 18 ppm.

Workers in the Installer/Decorator and General Foreman job categories were exposed to lower TWA CO concentrations, both with a GM of 7 ppm (1.4). The maximum 8-hour TWA for the Installer/Decorators was 16 ppm. The Attendants had a similar exposure distribution with a GM of 6 ppm (1.6) and a maximum TWA worker exposure of 17 ppm. Attendants exposures were not significantly different from Installer/Decorators' (Student's two-tailed t-test test, p=0.89).

The job category with the lowest exposures was the Desk Workers with a GM of 5 ppm (1.8), and a maximum of 10 ppm for one participant. Student's two-tailed t-tests comparing the combined Dock Foreman, Walker, Handyman, and Forklift Operator categories against the Installer/Decorators showed that they were significantly different (p=0.005).

TABLE 9

Moscone Center CO exposure survey summary statistics by date of measurement, job category, and job location. These data were collected using the LBNL/QGI CO Occupational Dosimeter and reflect time-weighted-average 8-hour workshift concentrations. Job category and job location are sorted by GM in ascending order.

| Category By Job | # obs (N) | AM[a] (ppm) | ASD[a] (ppm) | GM[a] (ppm) | GSD[a] | $90^{th}$ %-tile (ppm) | >25 ppm (%) | Max (ppm) |
|---|---|---|---|---|---|---|---|---|
| Desk worker | 4 | 6 | 3 | 5 | 1.8 | 9 | 0 | 10 |
| General Foreman | 7 | 7 | 3 | 6 | 1.5 | 10 | 0 | 11 |
| Attendant | 33 | 7 | 3 | 6 | 1.6 | 11 | 0 | 17 |
| Shop steward | 3 | 7 | 1 | 7 | 1.1 | 7 | 0 | 8 |
| Installer/Decorator | 49 | 7 | 3 | 7 | 1.4 | 10 | 0 | 16 |
| Supervisor | 11 | 8 | 2 | 8 | 1.3 | 10 | 0 | 11 |
| Rigger | 4 | 8 | 3 | 8 | 1.4 | 10 | 0 | 11 |
| Dock Foreman | 12 | 9 | 5 | 8 | 1.7 | 16 | 0 | 21 |
| Handyman | 6 | 10 | 6 | 8 | 1.8 | 19 | 0 | 20 |
| Dumpmeister | 2 | 9 | 0 | 9 | 1.0 | 8 | 0 | 9 |
| Forklift operator | 17 | 10 | 7 | 9 | 1.6 | 17 | 6 | 34 |
| Walker | 5 | 10 | 6 | 9 | 1.7 | 19 | 0 | 21 |
| Truck driver | 1 | 18 | NA | 18 | NA | NA | 0 | 18 |

[a]AM = Arithmetic Mean, ASD = Arithmetic Standard Deviation, GM = Geometric Mean, and GSD = Geometric Standard Deviation 3. Comparison of Parallel LOCD and Dräger Diffusion Tube Exposure Measurements.

Figure 20:
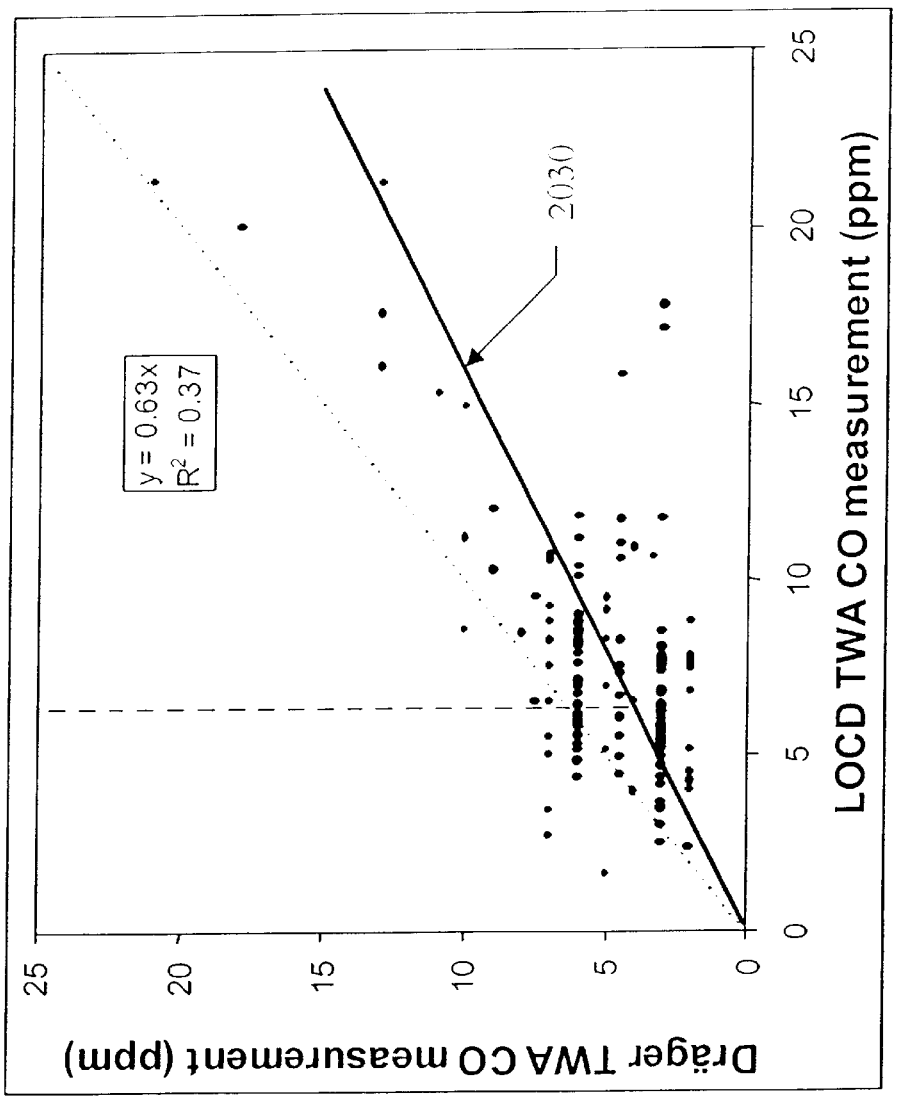
FIG. 20. Comparison between parallel 8-hour TWA LOCD and Dräger diffusion tube CO measurements from the MCC CO exposure study. The dashed vertical line represents the Dräger diffusion tube limit of detection of 6.3 ppm. The dotted diagonal line is a 45° line representing theoretical perfect correspondence between the two measurement methods.

FIG. 20 presents a plot comparing 8-hour TWA LOCD vs. Dräger exposure measurements conducted by Crawford for the 136 instances where both types of dosimeters were worn simultaneously by participants. The LOCD measurements were a subset of the 154 from which the data above are presented. Ten additional Dräger Tubes that had been paired with LOCD were lost because they dropped loose from their lapel clips during the workshift. Unfortunately, one important Dräger Tube sample that was lost was the mate to the highest LOCD measurement of 34 ppm worn by a Forklift Operator. Eight LOCD were deployed on participants without paired Dräger tubes.

The Dräger Tube data in FIG. 20 fall into discrete values relating to the graduated scale printed on the tubes. The lowest graduation on the tubes is 50 ppm-h which corresponds to an 8-hour TWA of 6.3 ppm (ie., 50 ppm-h/8-hr= 6.3 ppm). The discrete levels of Dräger data below 6.3 ppm indicate attempts at visual interpolation between zero and 50 ppm-h.

The overall scatter of Dräger data (Y axis) of FIG. 20 shows that the correlation between the Dräger data and the LOCD data was quite poor. A regression line (2030) for all 135 data points had a slope of 0.63 ($R^2$=0.37). A regression of the Dräger data below 6.3 ppm and their corresponding LOCD data had an even poorer correlation ($R^2$=0.44) and a slope of 0.61. When only the paired data Dräger Tube TWA value of 10 ppm or more were considered the slope was 0.80 ($R^2$=0.58). The average absolute value of the difference between the Dräger and the LOCD was 3.1±2.5 ppm. This can be compared to the similar statistic for the LOCD comparison to the bag samplers presented above which showed that the average difference between bag samples and individual LOCD measurements was 1.2±10 ppm.

Based on the results, the LOCD appears to have been able to provide considerably more accurate CO exposure data than the Dräger Dosimeter Tubes. The overall accuracy of TWA measurements of the Dräger tubes appears to be about ±3 ppm in the range of exposures whereas the LOCD accurate to about ±1 ppm. Based upon the comparisons with bag samples, the average of three LOCD samplers was in almost perfect agreement with the bag sampler. In contrast, the Dräger data were on average 60% lower than the LOCD, underestimating CO concentrations by about 40%.

This field study validated the use of the LOCD for occupational CO exposure assessment. The LOCD was able to withstand the rigors of workplace sampling without failing. 154 8-hour personal samples were collected on workshifts over three days. Exposure distributions were calculated with an estimated precision of ±1 ppm. None of the LOCD failed and only one was lost. The LOCD were used to compare results with the Dräger Diffusion Tube, a commercial industrial hygiene tool for monitoring workplace CO exposures. The comparison suggests that the Dräger device read about 40% low overall, and 20% low for observed TWA concentrations ≧10 ppm.

SUMMARY

The above described devices were designed and tested in the laboratory and the field. Laboratory testing proved that the devices could operate with precision much better than ±20%, usually below 10%. Bias of the devices was equally low ranging from 0–10%. The calculated accuracy of the LOCD ranged from 5–16%. Exposures at very high relative humidity may have lead to calculated accuracy up to ±27%.

Screening with high concentrations of a wide range of classes of organic and inorganic gasses indicated that the LOCD is resistant to many potential interferents. The exceptions were that the device is not selective against ethylene (positive interferent with and without CO) or nitric oxide (when CO is not present).

The LOCD was tested in the range of 10° C. through 30° C., and a temperature effect was found at 10° C. This finding indicates that the device requires a temperature correction in order to accurately assess CO exposures at temperatures lower than 20° C. This finding requires further investigation.

Both devices were successfully tested in preliminary field tests. The indoor air quality CO passive samplers PS1 and PS2 were tested in field settings, including residential settings and parking garages, where they performed within its design criteria. The LOCDs were tested in both small residential settings where they were exposed for several days, and in a large scale industrial hygiene exposure assessment survey where they were used to measure 8-hour workshift TWA CO exposures. Their performance was excellent in all of the field tests. They not only yielded accurate data as compared to concurrent bag sampler measurements, but they were simple to use and analyze, and they behaved reliably.

In conclusion, the results of this work are that the new technology using the palladium-molybdenum based MD15 sensors, configured into the passive diffusion sampler, has been proven to be a valuable device for measurement of CO exposures. In particular, the LOCD is a simple, reliable and accurate method for occupational exposure assessment.

What is claimed is:

1. A time-averaging carbon monoxide dosimeter, that measures integrated carbon monoxide concentrations in air, comprising:

a carbon monoxide sensor that changes optical properties as a function of carbon monoxide exposure, the sensor comprising a porous silica substrate coated with palladium and calcium chlorides, molybdosilisic acid, and sulfurous acid;

a sensor enclosure having at least two optically transparent windows to provide a means for monitoring an optical change of the sensor;

a photon measuring device selected from the group consisting of a spectrophotometer, and a simplified photon detection system, wherein the simplified photon detection system comprises a single- or dual-beam optoelectronic circuitry including at least one light emitting diode or laser diode, photodiode, a voltage sensing circuit, and a recording device for monitoring sensor optical change within a light spectral region of from 650 to 1,000 nanometers.

2. The device as recited in claim 1, further comprising a narrow tube attached to the enclosure for controlling the mass transfer rate of carbon monoxide to the sensor and corresponding dosimeter response to carbon monoxide exposure.

3. The device as recited in claim 1, wherein the sensor enclosure further comprises a color indicating silica gel and means for viewing a color change of the gel from outside of the enclosure, and wherein the enclosure further comprises one or more filter medium for controlling the relative humidity of the sensor and for removing potentially interfering chemicals.

4. The device as recited in claim 1 further comprising a narrow tube attached to the enclosure, and a desiccant with color indicator disposed within the enclosure.

5. The device as recited in claim 1, further comprising a removable plug attached to the enclosure to seal the device from exposure to outside air to control the time and duration of sensor exposure to carbon monoxide.

6. The device as recited in claim 1 wherein the porous silica substrate has an average pore size of from 40 to 500 angstroms.

7. The device as recited in claim 1 wherein the dosimeter has an accuracy of plus or minus one part per million, a linearity of response with a correlation coefficient of at least 0.97, a carbon monoxide exposure monitoring time in the range of from one hour to one week, wherein the dosimeter is reusable for at least one week, a sensor reversal of less than one percent per day, and wherein the device provides frequent measurements of optical sensor change to facilitate multiple sensor readings per day.

8. A carbon monoxide dosimeter for measuring the integrated carbon monoxide concentration in air comprising:

an enclosure having a hollow central chamber that is defined radially by an enclosure inside wall surface, and that is defined axially by a first closed end forming a chamber base, and a second open end forming a chamber opening;

an optically-responsive carbon monoxide sensor disposed within the enclosure;

a sensor housing disposed within the enclosure, wherein the sensor is disposed within the housing, the sensor housing including at least two optically-transparent windows for monitoring the sensor for optical change, wherein enclosure includes means for viewing the sensor for optical change;

a diffusion tube disposed axially within the chamber and extending from the sensor housing to the enclosure chamber opening, thereby forming an annular space between the tube and the enclosure inside wall surface, wherein the annular space is sealed off adjacent the chamber open end; and means disposed within the annular space for removing unwanted chemicals or moisture from air passed through the diffusion tube.

9. The dosimeter as recited in claim 8 wherein the sensor comprises a porus silica substrate that is impregnated with a mixture prepared by combining molybdosilisic acid, palladium chloride, calcium chloride dihydrate, and an acid selected from the group of sulfurous acid, hydrochloric acid, and mixtures thereof.

10. The dosimeter as recited in claim 9 wherein the porus silica substrate has an average pore diameter in the range of from 10 to 1,000 angstroms.

11. The dosimeter as recited in claim 8 further comprising a photon detecting means disposed adjacent the sensor.

12. The dosimeter as recited in claim 11 wherein the photon detecting means is a spectrophotometer.

13. The dosimeter as recited in claim 11 wherein the photon detecting means is a photon detection system comprising:

one of a light emitting diode or a laser diode;

a photodiode;

temperature compensated analog signal processing circuitry; and a data collection device to store sensor response readings, wherein the dosimeter is positioned adjacent the photon detection system so that the light emitting diode or laser diode, and the photodiode are at opposite sides of the sensor and directed towards respective optically-transparent sensor housing windows.

* * * * *

UNITED STATES PATENT AND TRADEMARK OFFICE
CERTIFICATE OF CORRECTION

PATENT NO.    : 6,607,700 B1
DATED         : August 19, 2003
INVENTOR(S)   : Apte et al.

It is certified that error appears in the above-identified patent and that said Letters Patent is hereby corrected as shown below:

Title page,
Item [73], Assignee, delete "Quantum Group, Inc.", insert -- Quantum Group Inc. --
Item [57], ABSTRACT,
Line 19, delete "precison", insert -- precision --

Column 38,
Line 36, delete "molybdosilisic", insert -- molybdosilicic --

Column 40,
Line 6, delete "molybdosilisic", insert -- molybdosilicic --

Signed and Sealed this

Second Day of August, 2005

JON W. DUDAS
*Director of the United States Patent and Trademark Office*